(12) United States Patent
Jimenez-Acquarone

(10) Patent No.: US 8,738,117 B2
(45) Date of Patent: May 27, 2014

(54) METHOD AND APPARATUS FOR PHYSIOLOGICAL ASSESSMENT IN MAMMALS

(76) Inventor: Isabel Jimenez-Acquarone, London (GB)

(*) Notice: Subject to any disclaimer, the term of this patent is extended or adjusted under 35 U.S.C. 154(b) by 1127 days.

(21) Appl. No.: 12/698,018

(22) Filed: Feb. 1, 2010

(65) Prior Publication Data
US 2010/0198092 A1 Aug. 5, 2010

Related U.S. Application Data

(60) Provisional application No. 61/148,895, filed on Jan. 30, 2009.

(51) Int. Cl.
*A61B 5/04* (2006.01)
(52) U.S. Cl.
USPC ................................................ 600/509
(58) Field of Classification Search
USPC ......................................... 600/509, 515, 519
See application file for complete search history.

(56) References Cited

U.S. PATENT DOCUMENTS

| | | | | |
|---|---|---|---|---|
| 6,508,771 B1 * | 1/2003 | Padmanabhan et al. | ...... | 600/515 |
| 6,937,888 B2 * | 8/2005 | Kohler et al. | ................ | 600/521 |
| 7,780,596 B2 * | 8/2010 | Kelly | ........................... | 600/437 |
| 2008/0004539 A1 | 1/2008 | Ross | | |

OTHER PUBLICATIONS

Clement et al.; "Heart rate fluctuations in the horse at rest: (2) Biological variation factors related to behavioural profile"; C.R. Acad. Sci. III; vol. 318, Issue 8; Aug. 1995; pp. 867-872.
Minero et al; "A note on reaction to novel stimulus and restraint by therapeutic riding horses"; Applied Animal Behaviour Science; vol. 97, Issue 2; May 2006; pp. 335-342.
Momozawa et al.; "Assessment of equine temperament by a questionnaire survey to caretakers and evaluation of its reliability by simultaneous behavior test"; Applied Animal Behaviour Science; vol. 84, Issue 2; Nov. 25, 2003; pp. 127-138.
Momozawa et al.; "Assessment of equine temperament questionnaire by comparing factor structure between two separate surveys"; Applied Animal Behaviour Science; vol. 92, Issue 1; Jul. 2005; pp. 77-84.
Physick-Sheard et al.; "Frequency domain analysis of heart rate variability in horses at rest and during exercise"; Equine Vet. Journal; vol. 32; 2000; pp. 253-262.
Rietmann et al.; "Assessment of mental stress in warmblood horses: heart rate variability in comparison to heart rate and selected behavioural parameters"; Applied Animal Behaviour Science; vol. 88; 2004; pp. 121-136.
Visser et al.; "Learning performances in young horses using two different learning tests"; Applied Animal Behaviour Science; vol. 80, Issue 4; Mar. 1, 2003; pp. 311-326.

(Continued)

*Primary Examiner* — Mark W Bockelman
(74) *Attorney, Agent, or Firm* — Patton Boggs LLP

(57) ABSTRACT

A method and tool for comparing mammals, such as horses, the tool including an electrode; an electronic heartbeat measurement instrument; an analyzer for determining an output indicative of adaptability, reactivity, or equanimity; and a plotting system for plotting the temperament parameter or temperament quotient on a grid. The tool is used to provide a value for the sympathetic nervous system index (SNSI), the parasympathetic nervous system index (PNSI), or the standard deviation of average mode normal to normal intervals (SDMNN). This value is correlated to a selected characteristic of the mammal.

8 Claims, 11 Drawing Sheets

(56) References Cited

OTHER PUBLICATIONS

Von Borell et al; "Heart rate variability as a measure of autonomic regulation of cardiac activity for assessing stress and welfare in farm animals—A review"; Physiology & Behavior; vol. 92, Issue 3; Oct. 22, 2007; pp. 293-316.

Biocom Technologies; "Heart Rhythm Scanner User's Manual" [online]; 1998; retrieved from the Internet at http://www.biocomtech.com/HRS%20Manual.pdf.

Bian et al.; "Nonlinearity degree of short-term heart rate variability signal"; *Chinese Science Bulletin*, Mar. 2004; 49:5, 530-534.

International Search Report in PCT Application No. PCT/IB2010/000211 dated Sep. 28, 2010, 9 pages.

Lippincott Williams & Wilkins; "Heart rate variability: Standards of measurement, physiological interpretation, and clinical use"; *Circulation*, Jan. 1, 1996; 1043-1065.

Visser et al.; "Heart rate and heart rate variability during a novel object test and a handling test in young horses"; *Physiology and Behavior*, Jun. 1, 2002; 76:2, 289-296.

\* cited by examiner

METHOD AND APPARATUS FOR PHYSIOLOGICAL ASSESSMENT IN MAMMALS

CROSS-REFERENCE TO RELATED APPLICATIONS

This application claims the benefit of U.S. Provisional Application No. 61/148,895 filed Jan. 30, 2009, which is hereby incorporated by reference to the same extent as though fully disclosed herein.

BACKGROUND

1. Field of the Invention

Embodiments of a system and method for physiological assessment in mammals relate generally to the field of physiological assessment of mammals and use of such assessments in selection processes such as breeding, monitoring effective training, and intervention, and in particular, apparatus and methods of assessing temperament.

2. Statement of the Problem

Horses are known to be complex animals capable of forming relationships with humans. Horses have been bred by humans for thousands of years. The ability to accurately evaluate the characteristics of horses has become of great importance. Many people, such as horse trainers, have spent their lives in the evaluation horses. A principal goal of such evaluation has been the selection of particular animals for racing, herding, and the general sociability with other horses and humans. Over the centuries, temperament has evolved as an important characteristic of horses.

As science has advanced, the temperament of horses has been the subject of much physiological study, research. and analysis. See Clement and Barrey 1995a; Physick-Sheard, Marlin et al. 2000; Momozawa, Ono et al. 2003; Visser, Van Reenen et al. 2003; Eager, Norman et al. 2004; Rietmann, Stuart et al. 2004; Momozawa, Kusunose et al. 2005; Minero, Zucca et al. 2006; and von Borell, Langbein et al. 2007. However, up to now, the evaluation of horse temperament, both by experts such as trainers and by scientific study, has been, at best, qualitative with non-repeatable results. Evaluation of characteristics of horses that is traditionally referred to as temperament remains at best an art, and some believe is still at the level of guessing and hunches. It would be highly useful if an objective measure of horse temperament were available.

SUMMARY OF THE INVENTION

Embodiments of a system and method for physiological assessment in mammals solve the above problems, as well as other problems of the prior art, by providing an objective measure of horse temperament. As will be discussed below, the systems and methods can also be applied to mammals other than horses.

The inventor arrived at an objective measurement of horse temperament by immersing herself in the science of horse physiology. After years of study, it became clear that one particular measurable parameter of horse physiology depended on a complex set of factors, including the horse brain, the horse nervous system, the horse musculature, and the horse cardiovascular system, all of which contribute to temperament. That is, the inventor realized that horse temperament is inherently a complex phenomenon; therefore, if it could be measured, it could only be measured by a parameter or parameters that are themselves the result of a complex system involving essentially the entire horse. The parameter that stood out as being complex enough to provide a measurement of temperament was the horse heart rate variability (HRV). The inventor resolved this objective measurement into three independent parts, which, for reasons that will become evident from the attached specification, she chose to call reactivity, equanimity, and adaptability, these three encompassing an animal's temperament quotient.

In this disclosure, for purposes of objectivity, temperament is defined as biologically rooted constitutional differences of an individual's behavioral tendencies, observed as reactivity, equanimity, and adaptability. For reasons that will become clear below, and even clearer on reading the attached specification, the sympathetic nervous system index (SNSI), as objectively measured by HRV, is equated to reactivity; the parasympathetic nervous system index (PNSI), as measured by HRV, is equated to equanimity; and the standard deviation of average mode normal to normal intervals (SDMNN), as measured by HRV, is equated to adaptability.

Reactivity is defined as showing a response to a stimulus or action in response to a situation as opposed to creating or controlling the situation. Upon consideration, it will be evident that how fast a horse's heart responds to stimulation has evolved as an important characteristic of a horse, both in survival in the wild as an animal that relied on flight to avoid predators, and in its ability as a race horse and as a work horse. Science has shown that the sympathetic nervous system is responsible for the neuronal and hormonal stress responses known as the "flight-fight" response. The sympathetic nervous system index (SNSI), as an HRV measurement of the function of the sympathetic nervous system, therefore, can be considered to be a measurement of the reactivity of the horse.

It is known that the parasympathetic nervous system in general inhibits or opposes the physiological effects of the sympathetic nervous system, as tending to stimulate the digestive secretions, slow the heart, constrict the pupils, and dilate the blood vessels, all associated with the rest functionality of the horse. Equanimity is defined to be calmness or composure, and it is not difficult to see this is an evolutionary function useful both in the wild and in domesticated horses. Thus, it is evident that the equating of the parasympathetic nervous system index (PNSI), as measured by HRV, to equanimity is reasonable.

Adaptability is defined as the ability to adjust or be modified by new conditions and uses. While adaptability can also be seen to be a useful function in both the wild and domesticated horse, its connection to an objective measure is perhaps not as understandable as the connection of the reactivity and equanimity. The inventor has equated this to SDMNN for complex reasons that will be understood from the attached specification. However, if it is understood that SDMNN is a long-term HRV phenomenon, then the connection to adaptability can more easily be grasped. The adaptability of an individual animal is its capacity to change from one state to another. This is correlated to the range of HRV measurements that the animal can produce. Ultimately, good adaptability is beneficial and shows a heightened capacity.

From the above, it can be seen that the inventor has developed a reasonable and understandable association of objectively measurable HRV parameters with temperament. As will be seen from the specification, the inventor has also developed reliable instrumentation for measuring reactivity, equanimity, and adaptability and software of analyzing the measurement results. In addition, the inventor has developed a multidimensional temperament grid in which the temperament of individual horses can be plotted. The inventor also has shown that the position of individual horses on this grid varies considerably; thus, embodiments of the systems and methods differentiate individual horses. While the measurement tool is new and unknown in science, it is evident from the above that the scientific basis for differentiation of individual animals is sound. It is evident that this tool can be used to correlate the differences with observed abilities of individual horses. Further, it is evident that a new tool for evaluating the temperament of horses has been provided.

In one embodiment, a method for assessing temperament in horses is given utilizing heart rate variability (HRV), the method comprising: determining for a horse a first HRV value indicative of the reactivity of the horse based on a HRV measurement, a second HRV value indicative of the equanimity of the horse based on the HRV measurement, and a third HRV value indicative of the adaptability of the horse based on the HRV measurement; and using the first HRV value, the second HRV value, and the third HRV value to characterize the horse's temperament. Preferably, the first HRV value is related to the sympathetic nervous system, the second HRV value is related to the parasympathetic nervous system, and the third HRV value is related to a standard deviation. Preferably, the first HRV value comprises the sympathetic nervous system index (SNSI), the second HRV value comprises the parasympathetic nervous system index (PNSI), and the third HRV value comprises the standard deviation of average mode normal to normal intervals (SDMNN). Preferably, the using comprises plotting the first, second, and third HRV values on a grid.

Another embodiment further provides a method for comparing mammals, the method comprising: making in a first plurality of mammals a HRV measurement, the plurality of mammals comprising a sufficient number of mammals of the same type to provide a scientifically valid sample; for each of the plurality of animals, finding from the mammal heart rate (HR) measurement a first HRV value; determining a first characteristic in each of the first plurality of mammals; correlating the first characteristic with the first HRV value for each of the first plurality of mammals to provide a reference standard; making a HR measurement in a second mammal that is not one of the first plurality of mammals, and finding from the measurement in the second mammal a first HRV value for the second mammal; and comparing the first mammal HRV value for the second mammal to the reference standard to determine the potential of the second mammal for having the first characteristic. Preferably, the first HRV value is a value that correlates with a parameter selected from the group consisting of reactivity, equanimity, and adaptability. Preferably, the first HRV value is selected from the group consisting of the sympathetic nervous system index (SNSI), the parasympathetic nervous system index (PNSI), and the standard deviation of average mode normal to normal intervals (SDMNN). Preferably, the determining comprises selecting the plurality of mammals from mammals having the first characteristic. Preferably, the determining comprises observing the first characteristic in the plurality of mammals. Preferably, the mammal type is selected from the group consisting of human beings, horses, dogs, camels, cows, pigs, sheep, and cats. Preferably, the mammal type is a horse and the first characteristic is an ability to win horse races, excel in competitions including endurance races, show jumping, dressage, and so forth. Preferably, the mammal type is a human being and the first characteristic is selected from the group comprising suitability for a sport, suitability for a relationship, suitability for a military assignment, effectiveness of training or intervention, organization of inmates, and selection for employment posts. Preferably, the method further comprises finding for each of the first plurality of mammals a second HRV value, the correlating comprises preparing a reference standard grid, and the comparing comprises determining the position of the HRV values for the second mammal on the grid. Preferably, the method further comprises finding for each of the first plurality of mammals a third HRV value, and the correlating comprises preparing a three-dimensional reference standard grid. Preferably, the finding comprises time domain analysis. Preferably, the finding comprises frequency domain analysis.

Another embodiment also provides a measurement tool for assessing a characteristic of a mammal, the measurement tool comprising: an electronic heartbeat measurement instrument capable of detecting the electronic pulses created by the beating of a mammal heart and outputting a heartbeat signal characteristic of the beating mammal heart; an electrode attachable to the heartbeat measurement instrument; an analyzer responsive to the heartbeat signal for determining an electronic output indicative of a temperament parameter selected from reactivity, equanimity, and adaptability; and a plotting system for plotting the temperament parameter on a grid. Preferably, the analyzer comprises a frequency domain analyzer. Preferably, the analyzer comprises a time domain analyzer. Preferably, the measurement instrument includes an electronic filter.

Embodiments of the system and method for physiological assessment in mammals provide an objective measurement of horse temperament. Now that this objective measurement has been demonstrated for horses, it is evident that it can also be useful for other mammals. It is evident that such an objective measurement can be useful for many purposes, such as evaluating individuals for particular sports or for different types of sports such as team and individual sports, evaluating individuals in schools where differences of individuals should be considered, in correctional institutions where conflicts between individuals must be managed carefully, in relationships, such as parenting or matchmaking, in research where comparative studies of individuals can provide useful information, for evaluating individuals for suitability for military assignment, monitoring intervention and training, selection for employment, and for many other purposes. It is evident that once a tool is provided, many uses may be found for it. Numerous other features, objects, and advantages of embodiments of the system and method for physiological assessment in mammals will become apparent from the following description when read in conjunction with the accompanying drawings.

DETAILED DESCRIPTION OF THE PREFERRED EMBODIMENT

In one embodiment, a system for determining temperament includes sensors for monitoring characteristics, a receiver for recording the characteristics of the autonomic nervous system, and a module for analyzing the recorded characteristics. The sensors monitor the autonomic nervous system of a mammalian subject. The measurement is compared to data from other known subjects to determine the temperament of the subject. By measuring characteristics of the autonomic nervous system (ANS), the temperament of the subject is determined. Examples of ANS characteristics that may be monitored include the HRV or cardiac electrical activity.

Figure 1:
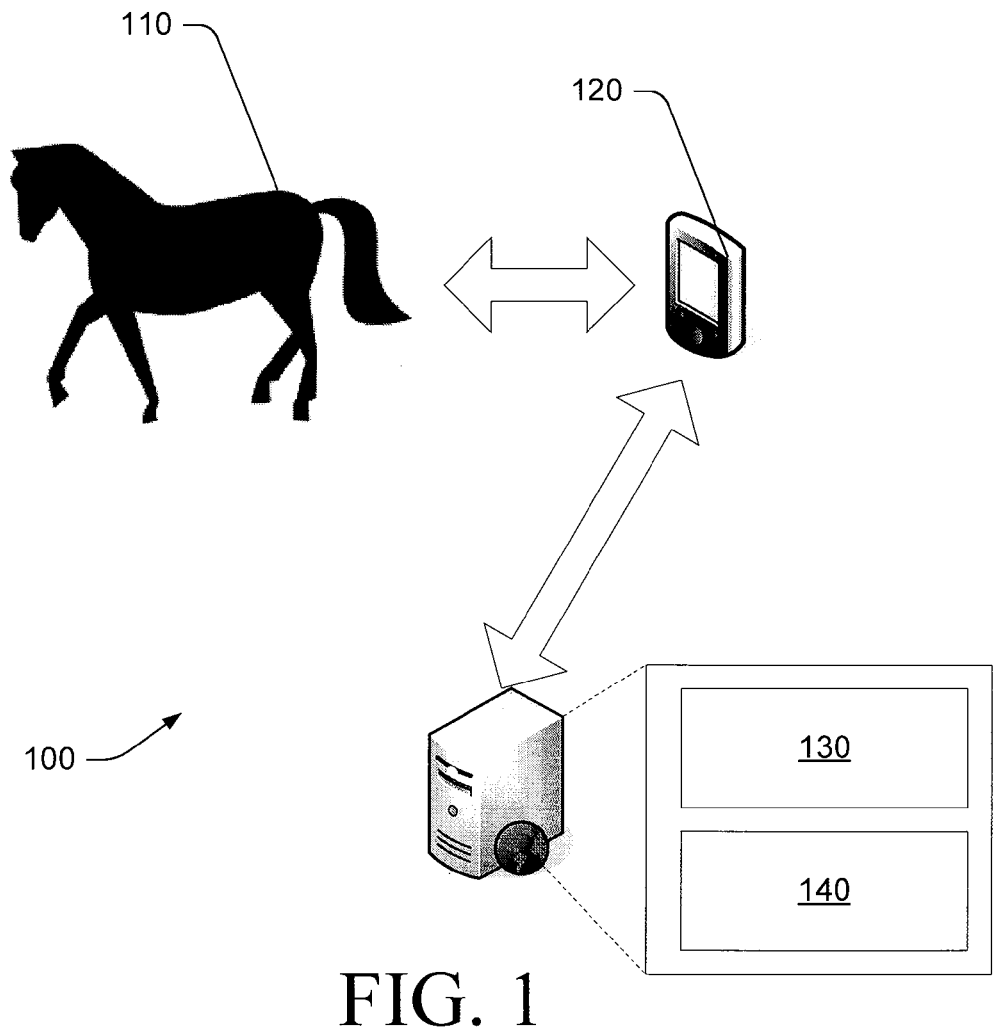
FIG. 1 shows one embodiment of a system for determining temperament.
Figure 2:
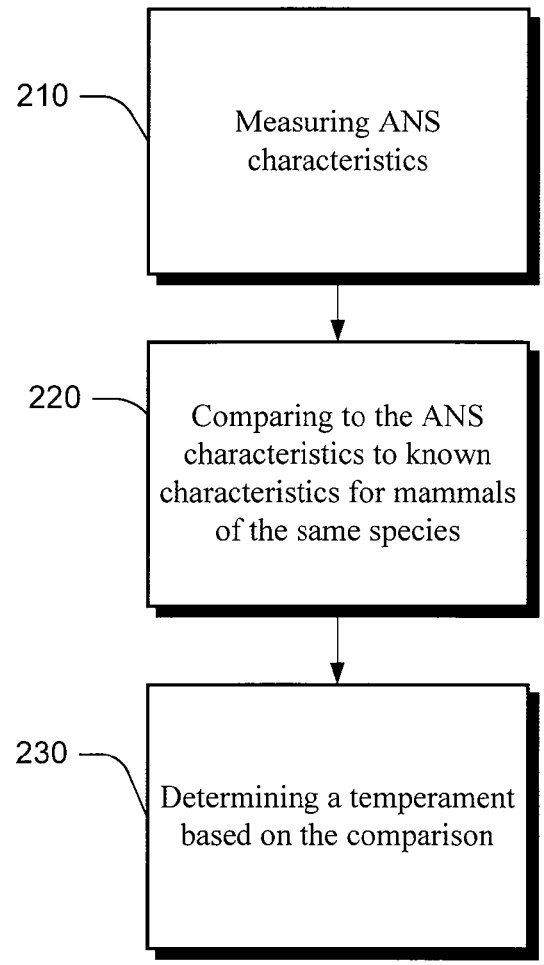
FIG. 2 shows one embodiment of a method for determining temperament.
Figure 3:
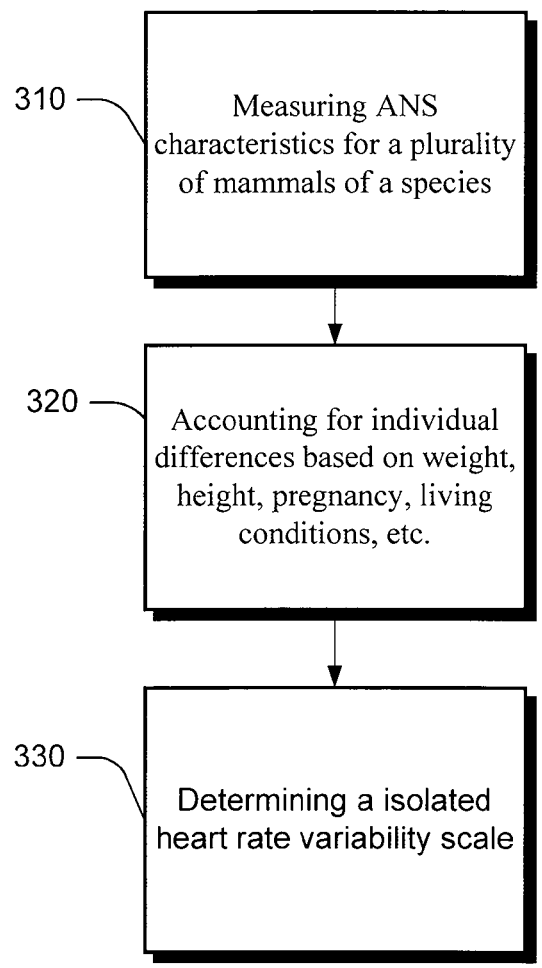
FIG. 3 shows one embodiment of a method for determining reference ANS characteristics.

FIG. 1 shows an exemplary system for determining the temperament of a mammal, including an ECG monitor 120 with three electrodes and a smart card for capturing data ECG located on animal 110, an analysis module 130, and a plotting system 140. Plotting system 140 may be omitted if a graphical representation is not desired. In an alternative embodiment, a telemetry transmitter located on a mammal, an ECG (also known by the abbreviation EKG) telemetry receiver, and an analysis module 130 is used. Various alternatives will occur to those skilled in the art based on this disclosure for capturing ECG data and providing it to analysis module 130. FIG. 2 shows an exemplary method for determining the temperament of a mammal including measuring ANS characteristics 210, comparing to the ANS characteristics to known characteristics for mammals of the same species 220, and determining a temperament based on the comparison 230. FIG. 3 shows an exemplary method for determining reference ANS characteristics, including measuring ANS characteristics for a plurality of mammals of a species 310, accounting for individual differences based on weight, height, pregnancy, living conditions, etc. 320, and determining an isolated HRV scale 330, wherein the effects of the environment and physical stature/condition of animals is accounted for and its effects on the scale limited.

Figure 6:
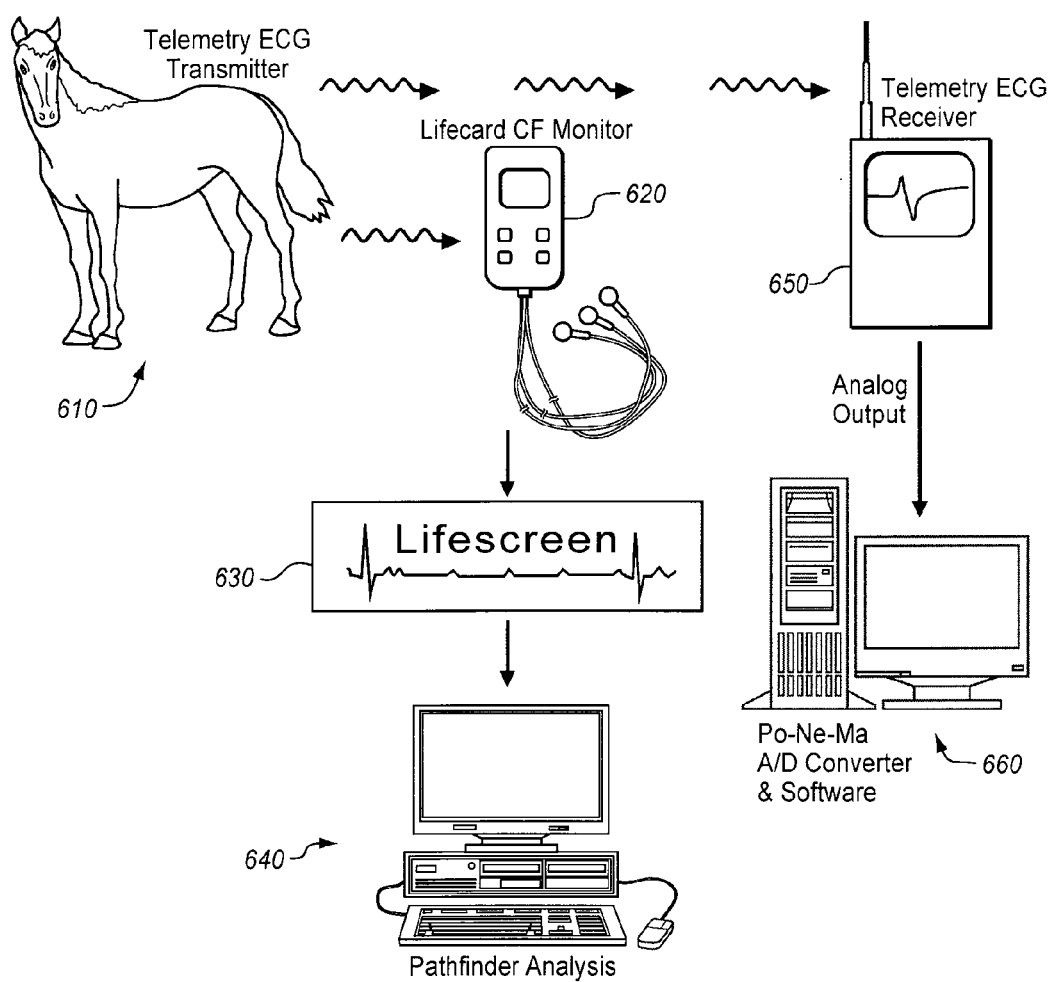
FIG. 6 shows two systems that can be used to interface with embodiments of heart rate variability (HRV) temperament prediction module.

FIG. 6 shows two systems that can be used to interface with embodiments of HRV temperament prediction module. A telemetry ECG transmitter 610 collects and transmits information collected from an animal the telemetry ECG receiver 650. Alternatively, a Lifecard CF monitor 620 collects data and stores it on a smart card. The Lifescreen Scanning Software 630 and Pathfinder Analysis 640 and Po-Ne-Ma A/D Converter and Software 660 analyze the signals received and provide them in a form available for the HRV temperament prediction module.

The ANS is the part of the nervous system that innervates smooth and cardiac muscle and the glands, regulating visceral processes including those associated with cardiovascular activity, digestion, metabolism, and thermoregulation. The ANS involved in the emotional component of behaviors acts as both integrator and modulator—integrating glandular function and somatic behavior, while modulating the intensities of the reactions of any behavioral response. Physiological changes accompanying emotional states are mediated by the ANS, which determines the nature of and is reflective of an animal's inner state and temperament per se.

Through the ANS, certain conditioned reactions determine the nature of future responses, which with little reinforcement may persist for years, and may result from the anticipation of a set of circumstances alone. Autonomic nervous system conditioned reactions are triggered by telereceptors, which are very fast, preceding somatic components of defense, alerting "fight or flight". In equine life, as well as the lives of other mammals, the ANS is involved in agonistic reaction, self-determination, survival efforts, comfort seeking, and preparation for future circumstances; and autonomic innervations improve acuity of olfaction, taste, hearing, touch, and proprioception.

The ANS has three major divisions: sympathetic, parasympathetic, and enteric; the first two are functional in regulating emotional behavior and homeostasis. The sympathetic division is responsible for the "fight or flight" reaction, the parasympathetic system is responsible for the "rest and digest" functions. In emergencies, when the body needs to respond rapidly to the external environment, the hypothalamus and the sympathetic nervous system activates an increased sympathetic outflow increasing heart rate (HR) and breathing rate and decreases digestive activity. Because sympathetic ganglia are closely linked, they act as a single system "in sympathy" with one another. The term "para" means beside or related to, and the parasympathetic system maintains basal metabolic rate under normal conditions; functions are related to and generally opposite to those of the sympathetic nervous system. The sympathetic and parasympathetic systems act in opposition, but are usually active at the same time to varying degrees, as at times parts of one system may be highly active along with parts of the other.

Effects of the parasympathetic nervous system and sympathetic nervous system tend to be opposite, and therefore antagonistic; organs are controlled by both systems in opposite directions (e.g., when the sympathetic nervous system increases HR, the parasympathetic nervous system decreases it). Each system uses different neurotransmitters; the parasympathetic nervous system postganglionic axons release acetylcholine (Ach) at synapses, and nerve endings spreading parasympathetic effects and nerve fibers are termed as cholinergic in their chemistry of neurotransmission. Postganglionic synapses of the sympathetic nervous system release noradrenaline, produced by the medulla of the adrenal gland, and nerve fibers are termed adrenergic. Noradrenaline release, at the adrenergic nerve fiber terminations, prepares for action and allows the animal the rapid "fight or flight" response. Sweat glands are an exception exclusively innervated by the sympathetic nervous system releasing ACh.

Sympathetic and parasympathetic pathways are tonically active, operating in conjunction with somatic motor neurons regulating normal behavior maintaining a stable internal environment in the face of changing external conditions.

The nervous and endocrine systems are clearly adapted for different roles; however, contact between the two systems is essential for their full function. The two systems are interdependent, cooperating through processes of neural secretion and the priming effects of hormones on the brain. These include the elaborate organization of interactions between individual activity, environmental stimuli received, and an animal's internal physiological state. All neurological command systems have amine-containing fibers: transmitters such as noradrenaline, dopamine, and serotonin all have a common feature, having small origins and widespread influences. Although the noradrenaline, serotonin, and dopamine systems are a small triumvirate located deep in the brain, they command and issue decisions throughout the whole brain.

The nervous system (both central and autonomic) is complex and chemically dependent, influenced by neuropeptides, hormones, and pheromones, which are in continuous communication throughout the body. Ongoing communication advises and instructs the individual organs on their physiological status and requirements of the animal as a whole, and appreciation of these chemical messengers is fundamental when considering behavior. Endocrine system effects are longer and are responsible for determining underlying predisposition (mood), while faster nervous system mechanisms relay emotions. It should be noted that the two systems are interdependent and impossible to separate when considering the concept of "temperament."

A neurotransmitter is serotonin, whose role is controlling aggressive behaviors. Such behaviors are linked with a decrease of brain serotonin turnover (in males) and linked to other factors including isolation and diet. Serotonin synapses inhibit behavioral impulses in areas of the brain that control punishment or unfavorable outcomes; high serotonin turnover results in restrained behavior, and low levels result in impulsive behavior.

Isolating animals causes drops in serotonin turnover; this is the amount of release and re-synthesis of a neurotransmitter by presynaptic neurons. An individual's brain which has low serotonin turnover may have a normal amount, but the neurons do not release serotonin or synthesize new serotonin to take its place, making it inactive. Lower serotonin turnover induces increased aggressive behavior toward other animals of the same species; the reverse also holds true, and increased serotonin turnover leads to friendly nurturing behavior. There were established differences in brain serotonin turnover among the groups of rats studied: "Friendly" rats showed an increased brain serotonin turnover rate, while "muricide" rats showed a modest decrease of brain serotonin turnover toward the rate that was evident in the "indifferent".

The amygdala, hypothalamus, brain stem, and autonomic system interact with the frontal and limbic cortex resulting in "emotional" experiences. Both pleasant and unpleasant stimuli result in dual effects, causing the amygdala to trigger both autonomic and endocrine responses integrated by the hypothalamus altering the internal state preparing for flight or fight, sexual experience, or another adaptive behavior.

The individual's internal reactions are primitive in origin and not under conscious control; however, once the animal interacts with its environment, another mechanism is activated. This second set, involving the cortex, modulates individual behavior. For example, even minimal proprioceptive feedback (e.g., from uneven ground) will adjust the central program for the individual's locomotion.

Although temperament traits were constructed using subjective methodologies, they can be objectively measured using variables that have a biological basis. Inhibition has been already positively correlated with HR, a relationship mediated by the parasympathetic nervous system, which dictates individual differences in reactivity and regulation. An integrated approach to temperament, which combines behavioral and physiological variables, results in a more accurate interpretation of an animal's state. Autonomic regulation of cardiac activity during emotional stress has not been extensively defined in farm animals, because investigations conducted outside the laboratory have suffered significant experimental constraints, limiting research.

Prior research on subjective states focused on behavioral (e.g., locomotor activity) and physiological (e.g., HR, corticosteroids, and adrenocorticotropic hormone) reactivity and ignored the neurophysiological processes (e.g., autonomic activity) that mediate these responses. Most studies incorporate measures of cardiac activity as a gauge of reactivity centered on simple time domain parameters and pay little attention to other more informative indices that give clearer insight into the activity of the ANS.

A horse's (or similar mammal's) perception (awareness of its environment) and its response or reactivity to sensations is an important indicator of temperamental state (or disposition). The horse's reaction is the expression, displaying its presence, status, and hypothetical intention, forming an important part of communication between horses, and providing an understanding of the individual's emotional state. An animal's reactivity is expressed through agonistic behavior such as aggression (fight), avoidance (flight), or submission, and will depend on the individual's dominance status.

Reactivity is the process by which an animal adapts to adjust, maintain, or restore internal harmony with the external environment in the face of unexpected changes. Reactivity ranges from simple defensive reflexes at spinal cord level to highly complex knowledge-based reactions from sensory information processed at the cortical level involving intelligence. Whether simple or complex, an individual's reactivity involves the ANS, a peripheral arm of the limbic system whose role is to establish homeostasis or physiological stability.

Panic behavior is linked with an over-responsive sympathetic nervous system, swinging frequently and rapidly between high and low stimulation of the heart and other organs. Physiological changes include increased blood pressure, expansions of the bronchial tubes, suppression of alimentary activity, and increased HR, thus ensuring good oxygenation of musculature for a rapid response reaction. The sympathetic part of the ANS is responsible for the modulation of emotions and expression of behavior.

Individual reactivity or "temperament" involves complex neuroendocrine mechanisms, which originate in the pituitary-adrenal system and is reflected by the individual's sympathetic nervous system. Hence, reactivity or "temperament" can be measured by the magnitude and quality of physiological changes including HR, i.e., HRV.

In one embodiment, a state of the art ECG monitor is used to detect HRV (see ECG Sensor 110 in FIG. 1). In alternatives, the electrical field of the heart is detected by a galvanometer (electrocardiography) attached to the body surface. Both the galvanometer and the ECG monitor record the potential difference between electrodes placed on the body surface at various points and detect the sum of electromotive forces present at any one time. Forces change in magnitude and direction from instant to instant during the depolarization—repolarization process. Factors affecting potential differences in diverse areas of the body include: shape of the thorax, position of heart in the body, pattern of activation within the heart, conductivity of the tissues between the heart and electrodes placed on the body surface, and exact location of the electrodes, all of which will influence the resultant ECG.

The ECG is a voltmeter measuring the resultant potential difference between two electrodes, and the link between a positive and negative electrode is known as a bipolar lead. Knowledge of electrophysiology of the equine heart is essential for the interpretation of electrocardiography because horses differ from most other species. Normal heart rate, known as "sinus rhythm", is governed by the sinoatrial (SA) node, a crescent shape structure located in the area where the cranial vena cava enters the right atrium.

The electrical impulse originates in the SA node and spreads across the atria to the atrioventricular (AV) node, along the specialized fibers leading to contraction of the atrial muscle and depolarization of both the right and left atrium. The depolarization of the myocardium initiates electrical activity, resulting in an electrical field detected at the surface of the body and recognized as a P wave of an ECG.

The AV node is located at the junction of the atria and ventricles in the interventricular septum (IVS) (also known as septum). When the AV node receives an impulse by electrical stimulation, it encounters a barrier to further spreading as specialized cells of this node have a high resting potential, poor electrical coupling, and a slow phase 0 depolarization resulting in a slow conduction of electrical impulses. Depolarization at the AV node involves a small number of specialized cells, not sufficient to cause either a marked difference in the electrical field or a visible deflection in the ECG, but observed as a delay in conduction between the P wave and the onset of the CARS complex.

In the horse, vagal tone and the parasympathetic system influence conduction through the AV node to the extent of sufficiently slowing or reducing conduction in amplitude. Reductions in the normal rate of conduction, or in some beats the complete obliteration and further spread of the impulse, is seen as a single P wave which is later followed by the start of another beat, and is recognized as a second-degree block. Histological differences are evident in cells of the AV node and SA node, the former having a slower rate of discharge than the latter; however, if the SA node fails to generate an impulse, the AV node takes over generating an impulse at a considerably slower rate.

Impulses travel through the AV node to specialized fast conducting fibers within the bundle of His branching both left and right further spreading through the myocardium in the Purkinje network. This network is widespread; and the depolarization of Purkinje fibers activates neighboring myocardial cells, resulting in rapid depolarization of the ventricles and their coordinated contraction. Depolarization of both the bundle of His and Purkinje network do not cause any deflection in the ECG; however, subsequent depolarization of the myocardium results in substantial electrical forces, producing the QRS complex. If both the SA and AV nodes fail to initiate an impulse, the Purkinje fibers are able to act as a pacing function, initiating an impulse at a considerably slower rate than that of both the SA node and AV node.

After depolarization, each cell repolarizes, and the sum of the repolarization processes within the heart can be detected in the electrical field at the body surface. The change in electrical field caused by atrial repolarization may be undetected; however, repolarization of the ventricles in the surface ECG is the T wave. T wave morphology is variable and dependant upon HR; changes are non-specific, and it is difficult to define a normal T wave. Changes vary between individuals and within an individual, as seen in horses in training who show more variability than their counterparts who are resting.

The electrical activity of the heart at the body's surface is the series of deflections described as P, QRS, and T waves. These waves and complexes are representative of the depolarization and repolarization of both the atria and ventricles. Electrocardiograms display the duration of intervals between waves and complexes; however, interval duration is dependent on conduction process and affected by autonomic tone and electrolyte levels. The identification of waves and complexes determines the occurrence of electrophysiological processes, while timing and duration provide information of the conduction process and HR per se.

The horse has an incredible capacity to increase its HR; its broad range is from resting 24-35 beats per minute to a magnum of 200-240 beats per minute (bpm) but has been found to vary between diverse horse breeds and use or disciplines. A combination of both HR and stroke volume influence cardiac output; and the stroke volume is dependent upon preload, afterload, and contractility.

Heart rate is controlled by both sympathetic and parasympathetic innervations, horses having higher vagal tones than humans. Parasympathetic synapses releasing the neurotransmitter ACh mediate equine vagal tone, which maintain a slow rate of discharge of the SA node and cause slow or intermittently blocked conduction of the AV node, resulting in low inotropic states. Adrenergic $\beta_1$ receptors mediate noradrenaline released from sympathetic fibers, causing a fall of the vagal tone and produce an instantaneous rise in HR and increased cardiac output.

Although changes in HR mediated by sympathetic fibers are slower than those of parasympathetic fibers, behavioral responses may alter and increase HR in anticipation of an event, while effects of humoral (catecholamine) components take several minutes to act and cause an increase in the inotropic state of myocardial cells. Changes in autonomic tone, which result in increased HR, are known as positive chronotropic responses; those resulting in a decrease in HR are known as negative chronotropic responses.

The rate of cardiac contraction in all mammals is influenced by nerve impulses from both central and autonomic nervous systems; however, the parasympathetic branch via the vagus nerve is primarily responsible for changes at the SA node and AV node. The parasympathetic influence stems from the neurotransmitter ACh released at the vagus nerve endings, which result in slow conductivity at the SA node and further cardiac impulses passing into the ventricles of the horse. Human studies found that the release of catecholamines at sympathetic nerve endings had the opposite consequence increasing cardiac output in certain emotional situations and in horses under extreme levels of exercise.

These factors can be "constant" or "flexible" across an animal's life. Rigid "constant" factors include sex or breed, while "flexible" factors are age, diet, use of horse, management, and/or environment. However, it is the combination of all factors that relate to the individual horse's behavioral response and is perhaps a reflection of its temperament.

Studies in the United States have found more cardiac diseases in male saddlebreds than in females; however, when considering baseline HRs, fillies showed a greater fluctuation in HRs (98 beats per minute) compared to male counterparts (83 beats per minute). Significant differences in HRs have also been found between breeds at exercise; for instance Anglo-Arab had lower HRs than half-breeds and French Saddle-Bred. The differences found between breeds were not stable across different situations or activities, as Andalusian horses initially showed lower resting HRs at exercise (15 and 20 km/h) and had higher HRs than both Anglo-Arabs and Arabians counterparts. Undeniably, breed is a strong influence on the horse in its use as an athlete or breeding animal and influences HR.

Wild horses have very similar diets; however, domestication, selection, and specialization (use) has led to tailored diets suiting a horse's individual needs and energy expenditure. The quality of feed and requirements of the horse are in a delicate equilibrium, calculated and balanced for optimal performance. Dietary supplements can provide beneficial effects on HRV, as in the case of yeast, which has been shown to produce lower resting HRs in performance horses. This study found lower HRs during the first five and final ten minutes of a 35-minute exercise workout for horses fed a diet with yeast compared to a diet without yeast.

Management, environment, and early handling influence an individual's HR; those with more handling experience have lower resting HRs and less marked increase in their HRs when confronting novel stimuli. Individuals housed in shared stabling show lower HRs than individuals housed in isolated stabling. Although certain environments or stressors, such as transporting horses, produce increased HRs, if horses are transported accompanied, the changes are less marked.

Individual disposition dictates HR; excited animals tend to have stronger pulses and higher resting HRs. Although HR is usually measured and monitored when individual animals have settled, in some cases excitable individuals may never settle, thus producing higher HRs than expected.

The normal heart does not beat at a constant rate but is continuously fluctuating and adjusting to the horse's metabolic requirements in its surrounding environment. Short-term and long-term fluctuations occur between periods of rest or work, exercise or stress, while longer fluctuations occur throughout the day and year.

Heart rate depends on the intrinsic rate of discharge of autonomic pacemaker cells of the SA node influenced by the ANS, and modulation of HR is gradual to sympathetic stimuli and rapid to parasympathetic stimulation. The ability of the vagus nerve in beat-to-beat regulation is the speed at which neural stimuli are transformed to cardiac response and the speed of removal after cessation of vagal activity.

Individual cyclical changes in HR are the pattern of variation on a beat-to-beat basis, which contains information concerning the contributions of both the sympathetic and parasympathetic branches of the ANS. However, cardiac modulation and degree of fluctuation of the HR is also adjacently under the control of regular impulses from baroreceptors in the aorta and carotid arteries. The heart's ability to respond to normal regulatory impulse which affects its rhythm is reflected in the HRV.

Heart rate variability research focuses on quantifying the variance of the ECG signal of a periodic process as the heartbeat, and the peak of the process "R" wave is known as the amplitude. The arithmetic relationship between amplitude and variance states the square of the amplitude divided by two is equivalent to the variance [variance=(amplitude)$^2$/2]. Therefore, allowing the decomposition of physiological processes (HRV) into sine waves provides a method of describing component variances of the different periodic processes such as a heartbeat. The duration of a sine wave defines the period and the reciprocal of the period defines the frequency, providing the basis for spectral analysis.

Time domain and frequency domain are two approaches used to describe and analyze periodic components of a heartbeat time series in the study of HRV, and both methods provide valuable tools to describe periodic phenomena of HRV.

Time domain methods are non-spectral methods used to quantify HRV, they are reported in units of time, and can be categorized by their mathematical techniques as either statistical or geometric. Unlike frequency domain analysis statistical methods, time domain methods rely on mathematical equations which do not reflect any physiological mechanisms. Time domain representations plot data as a function of time and are relevant to the study of periodic processes based on the autocorrelation function which is the correlation of one time series with a time-shifted version of itself (mathematical extensions of traditional correlation techniques).

Originally, HRV was assessed manually from calculations of mean RR intervals, and their standard deviations (SD) were based on short time frames of five minutes with calculations of smaller standard deviations meaning lower HRV. There are over 26 different types of arithmetic manipulations of RR; and all methods appear to be largely equivalent in merit, providing ECG measurements are 5 minutes or longer. However, each technique has a suggested minimum ECG recording length to ensure correct statistical analysis and representation of the time domain measure. The techniques require an initial processing to remove artifacts and non-sinus beats using a combination of computer processing and human editing, then the remaining RR intervals of sinus origin are measured and subjected to statistical analysis. Calculations based on time domain analysis can be performed over a wide range of lengths of recordings from a suggested minimum recording of at least 1 hour and up to 24 hours.

The most common time domain method is the standard deviation of all normal intervals (SDNN), derived from a histogram of RR duration against number of RR intervals for all RR intervals in the 24-hour period calculated. The variance of this measure is equal to the total power of spectral analysis and is proportional to the total power of the power spectrum, and SDNN reflects an overall variability of the heart. The difficulty in obtaining long recordings of 24 hours with sufficient quality has led to a suggested minimum length of 4 hours for SDNN analysis.

Another commonly used statistical variable calculated from segments of the total monitoring period includes the standard deviation of the average NN interval (SDANN) calculated over short periods, usually 5 minutes, which is an estimate of the changes in HR due to cycles longer than 5 minutes. Two domain measurements which are estimates that reflect the HF band of the power spectrum include both the roots mean squared of successive intervals (RMSSD) and the percentage number of intervals greater than 50 ms (pNN50). The 50 ms interval, the number of mean daytime hourly counts of pNN50 in normal horses, suggests that horses have more variability in HR than a human. It is inappropriate to compare HRV results derived from different time durations, as the length of the signal that is sampled significantly influences variability.

Time domain statistical procedures describe periodicity and are extremely useful when the time series is characterized by a relatively pure sinusoid uncontaminated by other random influences. Time domain techniques are recommended for long-term recordings; they can also be used when only short periods of sinus rhythm exist or for short-term recordings for physiological studies. The "lag" of a time series represents the displacement in terms of time sampled sequential data points as a characteristic of a deterministic time series and is not representative of physiological and behavioral periodic processes and, therefore, initially deemed unsuitable HRV methods for assessing equine temperament.

Frequency domain methods, also known as spectral analysis, distinguish between the intrinsic source of HRV occurring at different frequencies. Spectral analysis transforms a sequence of data values in the time domain into a sequence of frequency values. The spectral analysis based on "Fourier transform" states any continuous sequence of data values in the time domain can be equally represented as the sum of many waves of different frequencies, amplitudes, and phases. This allows a sequence of data values in the time domain (a sequence of RR values) to be transformed and represented as a spectrum in the frequency domain.

In Fourier analysis, each frequency (i.e., wave) has two components: its amplitude (or strength) and its phase (whether the wave starts at its maximum, minimum, or somewhere in between). The phase of the frequencies is of no interest and removed by squaring the Fourier analysis components for each frequency resulting in a "power" value for each frequency, with the sequence of powers per frequency giving the power spectral density (PSD) function.

In a sequence of regularly sampled data values in the time domain, the longest and shortest possible wave can be calculated using Fourier analysis. The longest wave is half the duration of the data sequence in the time domain, and as the frequency of any wave is the inverse of its wavelength, the smallest frequency is fmin=1 I(T/2)=2/T. Where fmin determines the minimum of x and y, I is the inverse and T is the duration of the data sequence in the time domain. The highest frequency calculated from any regularly sampled sequence of data values in the time domain is known as the "Nyquist frequency", which is half the sampling frequency of the data values in the time domain.

The Fast Fourier Transformation (FFT) is a mathematical algorithm performing a discrete Fourier analysis on a sequence of regularly sampled data values in the time domain and is suited to running quickly on a computer. However, the mathematics of the FFT process requires the number of input samples to be an exact power of 2 (e.g., 2, 4, 8, 16, 32 ... 256, 512, 1024, etc.). The number of data samples analyzed from any period is given by the period duration times the sample rate. If the value is not an exact power of two, "zero-padding" is used to increase the number of samples to the next highest exact power of two. A zero-padded FFT analysis produces slightly different PSD spectra than a non-zero padded exact mathematical Fourier transform. This is only superficial, as the zero-padded FFT simply calculates more frequency samples when describing exactly the same frequency spectrum.

Once the PSD spectrum for an RR sequence is generated, a spectral analysis simplifies the spectrum into the set of "Frequency band power values". The power value for each band used is given by the area under the PSD spectrum between the lower and upper frequency limits of that band.

Frequency domain analysis detects the occurrence of rhythmical changes in ECG recordings and measures the amount of cyclical variation occurring at different, physiologically important frequencies. There are three frequency domain power bands in spectral analysis of human HRV analyses:

High frequency (HF), mediated via the vagal nerve due to ventilation.

Low frequency (LF), mediated by the vagal and sympathetic nerves.

Very low frequency (VLF) influenced by posture, which can be further divided into an ultra low frequency (ULF) and solely assessed on 24-hour calculations. Mechanisms controlling the ULF are unknown, although the Renin-Angiotensin-Aldosterone System (RAAS) is a suggested physiological system.

Overall Total power (Total) is defined as VLF+LF+HF.

In horses, frequency and spectral bands are measured in hertz (Hz) and determined as:

VLF 0 Hz to 0.01 Hz
LF 0.01 Hz to 0.07 Hz
HF 0.07 Hz to 0.5 Hz
Total 0 Hz to Nyquist limit (i.e. all frequencies)

Heart rate accelerations or decelerations occurring over short (2-4 cycles) RR interval sequences are principally parasympathetically mediated, while accelerations or decelerations occurring over long (8-30 cycles) RR interval sequences are predominantly sympathetically mediated.

The number and amplitude of long-term changes measured provides qualitative information of change in the sympathovagal balance, an index known as LF/HF ratio. The calculation of LF/HF ratio provides an index for sympathovagal balance and an idea of the direction and magnitude of reciprocal changes in autonomic activity. Normalized units (nu, percentage value over total power after subtracting of the LF power) are used to study each component in detail. Both in humans and animals, functional states likely to be accompanied by increased sympathetic activity are characterized by shifts in the LF/HF balance in favor of the LF component; and the opposite occurs during increases in parasympathetic activity. It is generally considered that LF/HF ratio is better studied in conjunction with LF and HF referents from which they are derived.

Parasympathetic activity expresses itself up to frequency ranges higher than the ones reached by sympathetic activity. The influence of the parasympathetic nervous system affects HR over a broad band of frequencies, encompassing all the frequency domains. The amount of LF and HF components in the RR interval time sequence and the ratio of LF/HF used to study the ANS regulation and parasympathetic nervous activity in the horse have shown the HF variation period is between 2 and 10 heartbeats and the LF variation period is between 15 and 100 heartbeats. Consequently, HF variability detected is a good indicator of parasympathetic activity, except at very low breathing where the respiratory component is solely mediated by vagal activity; consequently, HF spectral power is used as an index of cardiac vagal tone. LF activity reflects cardiac sympathetic activity, and past research has shown that the sympathetic nervous system has shown to be of little influence in the resting horse.

Certain short-term intrinsic fluctuations in HR are coupled with internal regulatory mechanisms such as respiration and blood pressure (BP) regulation occurring at specific frequencies closely relating to their physiological functioning system. The respiratory cycle, or the respiratory sinus arrhythmia, corresponds to HR variations found in the HF range and is known as the respiratory peak mediated by the parasympathetic nervous system. Autonomic activity indicators are known as the Sympathetic Nervous System Index (SNSI) and the Parasympathetic Nervous System Index (PNSI) which are calculated using the following frequency power bands: SNSI=LF/HF and PNSI=HF/Total.

If the HR time series units are beats/second, then the resulting power spectrum units are seconds$^2$/Hz. The power in a band is in units of seconds$^2$; however, the power in a band is often converted to units of ms$^2$. Normalized units are dimensionless; the power in a band can be expressed as a fraction of total power.

All of the HRV indices described above, except pNN50, have units of time (ms) and thus, strictly speaking, are measures of variability in the RR interval, not HR. HR and RR intervals are reciprocals of each other, where HR has units of beats per minute (bpm) and RR has units of ms. Fluctuations in RR interval and HR are closely related but not in a linear way, since the reciprocal is not a linear operation. Thus, a doubling in RR interval variability does not mean HRV would necessarily double if measured from the sequence of corresponding instantaneous HR values. Time domain measurements are calculated from the RR (or NN) interval sequence, even though instantaneous HR may be more closely tied to autonomic tone and, therefore, have greater physiologic significance than the RR interval.

The units of HRV parameters are often not cited, making it difficult to compare parameter values across studies. If the input series contains values in beats per second, the power spectral density function has units of seconds squared per Hz, and the units of power are seconds squared, often converted to milliseconds squared (ms$^2$) to bring the numerical values into a reasonable range.

Spectral analysis of HRV is a quantitative, reliable method for analyzing the modulatory effects of neural mechanisms of the sinus mode. However, accurate assessment by frequency domain analysis requires that the HR data exhibit stationary (as subtle changes can mask sympathovagal changes), multiplicity, and symmetry plus absence of artifact.

Fourier analysis requires the input data to be sampled at regular time intervals; irregularly sampled sequences first must be re-sampled into an equivalent sequence which is further sampled at a constant rate (or frequency) before performing Fourier analysis.

An RR interval is measured the instant the terminating heartbeat occurs, and RR intervals are not equal; thus, resulting RR intervals are irregularly sampled sequences, which are re-sampled into an equivalent regularly sampled sequence before spectral analysis is performed. Re-sampling times are not at the same times as the heartbeat times, and "interpolation" methods are used to obtain RR values at times between heartbeats.

The simplest method of re-sampling interpolation is "sample and hold", where the RR interval between any two heartbeats is set equal to the RR value of the first heartbeat. However, this method is discarded as resultant abrupt "step-like" changes from one RR value to the next cause Fourier analysis to overestimate HF components of the entire sequence (thus, abrupt-looking changes in the RR graph contain numerous HF components).

Two methods of re-sampling interpolation include "linear interpolation" and "cubic spline interpolation". Linear interpolation estimates an RR value at any given time between two heartbeats by drawing a straight line between the RR values of the two heartbeats and using the value of the line at the desired time as the estimated RR value. Cubic spline interpolation and linear interpolation methods are similar, other than the line drawn is not straight but curved. In cubic spline, the shape of the curve depends on how RR values change in the adjacent region around a given time, with the value of the curve at the given time providing an approximate RR value. Research has found that generally cubic spline interpolation calculates more accurate spectral analysis than their counterparts and, therefore, is employed in embodiments of the system for determining temperament.

Cubic splines can act erratically where there are gaps in the RR data in the adjacent region about the given resampling time. However, the Del Mar. Reynolds Medical HRV Tools software program used provides a "gap-filling" function using linear interpolation to add additional pseudo-RR values when the "maximum gap length" is surpassed, curtailing erratic cubic spline behavior. The "maximum gap length" can be defined, enabled, or disabled by the experimenter according to the data collected and was calculated and permanently set. Cubic splines may act erratically near sudden abrupt changes in the local HR indicative nonstationary data; however, it is rare for such data to be present in a HRV analysis. The overall effect of the cubic spline method in relation to such abrupt changes on the resultant spectral analysis is much less than the actual effect of the abrupt change itself.

Aliasing occurs during re-sampling if the maximum (Nyquist) frequency is lower than that of the highest frequency component present in the re-sampled data sequence. The Nyquist frequency is half the re-sampling rate; the re-sampling rate has a direct relationship with potential signal aliasing. To avoid aliasing, re-sampling should be at a frequency more than twice the highest frequency present in the initial data, and/or the initial data is filtered so all higher-frequency components are removed before resampling.

The Fourier analysis of a time series is the decomposition (a periodogram) of the series into the sum of sine and cosine terms and is the finite Fourier transform of the autocovariance function. The periodogram is easy to calculate; but it does not provide consistent estimators for the spectral densities and requires further methods to "smooth" the periodogram providing spectral density estimates with less bias and variance. Spectral analysis use "smoothing" methods or windowing, which augment the description of stable estimators with stochastic processes. The objective of the windowing technique is to minimize the bias and variance and "smooth" the spectral density function derived from the Fourier transform.

Windowing implemented in frequency and time domain methods is by summing the weighted spectral density estimates on both sides of a specific frequency of interest. Abrupt shifts in a spectrum (periodogram) represent unstable estimates; by stepping a weighted function, these become more stable. Spectral leakage is the consequence of the finite duration of the RR data sequence input to the Fourier analysis and is the translation of power from one frequency to adjacent frequencies above and below the actual frequency. Although the Bartlett windowing is recommended for FFT on segments of data providing one smooth spectrum, frequency domain smoothing affects the width of the peaks; and the overlapping of spectral density estimates across a certain range of signals. In many embodiments, Hamming "windowing function" was chosen and applied to data before performing the Fourier analysis on the data sequence. Hamming windowing enhances statistical properties of both discrete Fourier transform and the FFT.

An important point of spectral analysis is the requirement for "stationary" data. A sequence of stationary data contains pure (and infinite) periodic components rather than aperiodic components which are non-stationary. If numerous significant aperiodic components are included, then the Fourier analysis is prone to significant error. No real RR data sequence is infinite; therefore, there is never complete stationarity of RR data. Unavoidably certain aperiodic (non-stationary) behavior occurs in RR traces, including increases in HR; therefore, for practical purposes wherever possible, clear non-stationary data is avoided.

Heart rate variability analysis research includes the removal of all non-sinus beats from the RR sequence prior to an analysis, as these beats are non-stationary. However, the significance of the second-degree AV blocks in the horse as a regulatory parameter warrants further investigation into their inclusion/exclusion in HRV analysis measurements. Another aspect of stationarity is "coherence length"; as the duration of the analyzed RR sequence increases, there is a probability that the higher frequency components retain the same phase as they started with decreases. In RR data, coherence length is the duration over which the phase of a given frequency component is constant and, once exceeded, the Fourier analysis starts to average frequency components which are out of phase with each other, the net effect being that the magnitude of those frequency components measured by the Fourier analysis decreases. When a long duration RR sequence is analyzed using Fourier analysis, the higher frequency components become less consistent and tend towards zero. Given the length of sequences influences the frequency components, the effects are different length ECG recordings on equine HRV analysis frequency domain, SNSI, and PNSI parameters.

This removes non-stationary slow-moving trends from the RR data before the Fourier analysis. The RR intervals of an ECG often exhibit a non-stationary trend, as aperiodic activities such as waking/sleeping, feeding, and so on occur during recording. To control spectral leakage, a windowing function is applied to the re-sampled data before the FFT is performed; however, this function can distort VLF waves into appearing as if they were higher frequency waves.

Before applying windowing functions, the re-sampled data is detrended first by one of two methods: "linear" or "mean" subtraction. In "mean subtraction", the average value is subtracted from all of the re-sampled RR values before the window function applied, while "linear subtraction" (the best-fit straight line using a least mean square rule) is subtracted from all of the re-sampled RR values before the windowing function is applied. The "linear subtraction" detrending method was used in many embodiments as it removes not only the baseline (mean) RR value, but also any very gradual slope exhibited by the RR sequence over its duration. This detrending method is superior to the "mean subtraction" method, as it does better at removing very long period drifts that are almost always present.

The SA node is the primary source of electrical impulse, which generates the ECG waveforms. Additional latent pacemakers exist throughout the heart, particularly the AV node and the Purkinje tissue. These may give additional electrical impulses, which will appear as ectopic beats. Therefore, disturbances due to either abnormal impulse formation or impaired conduction gives rise to extra electrical wavelets or non-sinus beats, interfering with RR analysis. Since modulatory signals from the brain to the heart are embedded as variations in the beat-to-beat intervals of sinus rhythm, a locally generated aberrant beat will appear to temporally disrupt neurocardiac modulation. The ectopic beat, which is often premature, produces a short beat-to-beat interval followed by a compensatory delay, i.e., a longer than normal interval. This will lead to a sharp transient increase in HRV.

Ectopic beats appear in normal healthy horses and thus represent a major source of error when analyzing HRV data. Although HRV is used to assess beat-to-beat variability of the normal sinus rhythm, AV block is a physiological mechanism mediated by the vagal nerve; and the use electronic filters leads to the exclusion of misdetected RR intervals. The use of filters in the horse reduces the time spent checking data and achieved by setting to calculate intervals, which differ by between 65% and 175% of the preceding interval, and filtering effect on HRV measurements needs to be investigated further. At present, the inclusion of blocked beats in HRV calculation does not allow the comparison of results with those from other studies; thus, the inclusion of blocked beats and their effects on HRV analysis needs to be considered.

The advantage of geometric methods is that they provide an assessment of HRV even when the quality of data would exclude the use of spectral or statistical methods. These techniques involve converting a series of NN intervals into a geometric shape, because the geometric shape can easily be mathematically filtered. The disadvantage of these techniques is that they require a greater number of NN intervals to construct a representative pattern and offer little information for physiological studies with time intervals for recordings less than 30 minutes. Geometric techniques offer potential for use with horses in clinical settings where long-term recording is less than ideal; however, few studies have employed such methods.

Two common geometric methods include the triangular index (and amplitude distribution curve of NN intervals) and Lorenz plots (NN intervals can be plotted against the preceding interval, and the geometric shape will define the variability). Both geometric methods are influenced more by lower rather than higher frequencies of the power spectrum, and the shape of the plots gives a qualitative rather than quantitative assessment of HRV.

The Triangular or St Georges index is justified when a compact quantitative representation of a more complex set of data is produced, or attention is drawn to, or emphasizing an important component in the data. However, the Triangular or St Georges index has not been fully investigated in the horse, and varied research results have not produced indices and parameters for valid comparison.

A number of analytical techniques can be used to demonstrate non-linear behavior in biological systems. A phase plane plot is representative of the behavior of a dynamic system and is usually a graph of the position of a signal on one axis versus the velocity of the signal on the other. HRV data produces a "return map", which is similar to the phase plot but uses data in a discrete digital form. The return map represents the relationship between a point and any subsequent point in a time series and takes the form of a graph in which each RR interval is plotted on the X-axis against the preceding RR interval on the Y-axis. This graph is known as a Lorenz plot, where the width of the scatter demonstrates significant agreements with other indices of autonomic function. In spite of widespread interest, absence of studies in horses limits the clinical application of the technique; and cross-comparison of studies and these techniques are not likely to supersede spectral analysis in the short term and give a qualitative assessment of HRV. However, Lorenz plots have demonstrated significant agreement with other indices of autonomic function, favoring the use of this method when investigating HRV as a method to assess temperament and the underlying behavior of a dynamic system such as the equine heart.

In 1996, both the European Society of Cardiology and North American Society of Pacing and Electrophysiology standardized the use of HRV in humans; however, there has been no similar standardization in horses. The absence of standardization, validity, reliability, and cross-comparative studies has meant that HRV has been under exploited as a tool to assess autonomic control of the equine heart. Reliability of any method of analysis of HRV depends on the recording of a representative ECG of sufficient quality, which can be analyzed by suitable algorithms to identify R waves and, thus, calculate accurate RR intervals. The detection of components of the ECG by digital monitors is usually based on the sequence, shape, and size of the waveforms, while analog systems require detection by shape recognition of waveforms with variable amplitude thresholds. The accurate detection of R waves is essential, as misinterpretation of normal waveforms lead to large errors in HRV results, especially when using frequency domain analysis.

Although rigorous monitoring excludes these errors, the collection of an adequate quality recording overcomes some of these problems. Physiological mechanisms do not bring about sudden changes in RR intervals; and large differences are likely to be due to environmental "noise", prematurity, or poor detection of complexes, and automated methods for filtering the RR signal produce acceptable results. Before using HRV to assess equine temperament, standardized equine HRV parameters need to be established.

Heart rate variability is a non-invasive method, which appears to provide an insight into an individual's autonomic function and balance. HRV is an objective measure of an individual's emotional state assessing interactions taking place between physiological, emotional, mental, and behavioral processes.

Low HRV has been linked to behavioral problems as anxious animals exhibit low indices. Similarly, animals previously exposed to stress consistently had lower HRV indices than animals who where never stressed, even when no longer exposed to the stressor. Anxiety and stress response in animals is independent of breed, age, sex, conformation, HR, blood pressure, and respiration rate, but dependent on individual temperament.

Heart rate variability analysis allows a greater understanding of the neurophysiological regulation of stress responses (or reactivity) in horses or other mammals and is achieved by non-invasively measuring both short-term and long-term cardiac activities via ECG. When practically applied, the information allows the researcher to evaluate or assess the horse's internal state or temperament, reflecting the impact of its current environment and present requirements on the animal.

Temperament is in HRV per se.

Before using HRV as a means to assess temperament, several criteria must be investigated and the methodology standardized: First, equipment must be validated and the effects of filtering and time intervals on sampling established, thus standardizing HRV analysis methods. Given that HRV is the study of sinus rhythm, and normal horses have AV second-degree block, the decision as to whether to exclude or include beats' effects must be determined. Once these initial variables have been considered, another fundamental factor to determine is whether the time of day has an effect on data collection and results. When defining HRV as a measure of temperament, it must be clear that differences in these measures cannot be attributed to other factors such as sex, age, training, etc. HRV establishes how temperament can be determined from HRV measures and what the biological parameters are indicative of in an individual.

Various filters and analysis interval lengths using the RR interval in normal horses (i.e., in the absence of ectopic beats and second degree AV blocks) on frequency domain variables and sympathetic and parasympathetic index values may affect the analysis. Furthermore, differences in chosen time intervals and time intervals effectively reflect changes in the internal state of an individual horse represented in changes in both the sympathetic and parasympathetic branches of the ANS. In one embodiment second degree blocks are included in the analysis of the HRV. In animals such as horses this may be an advantageous choice, since second degree blocks are typically the result of high vagal tone in horses. Second degree blocks in horses may be similar to the control mechanism in humans that brings about respiratory and sinus arrhythmia is humans. In an alternative second degree blocks are excluded. This may be an advantageous choice in animals such as humans and dogs since these blocks may be indicators of disease and may not be indicative of temperament.

Figure 7:
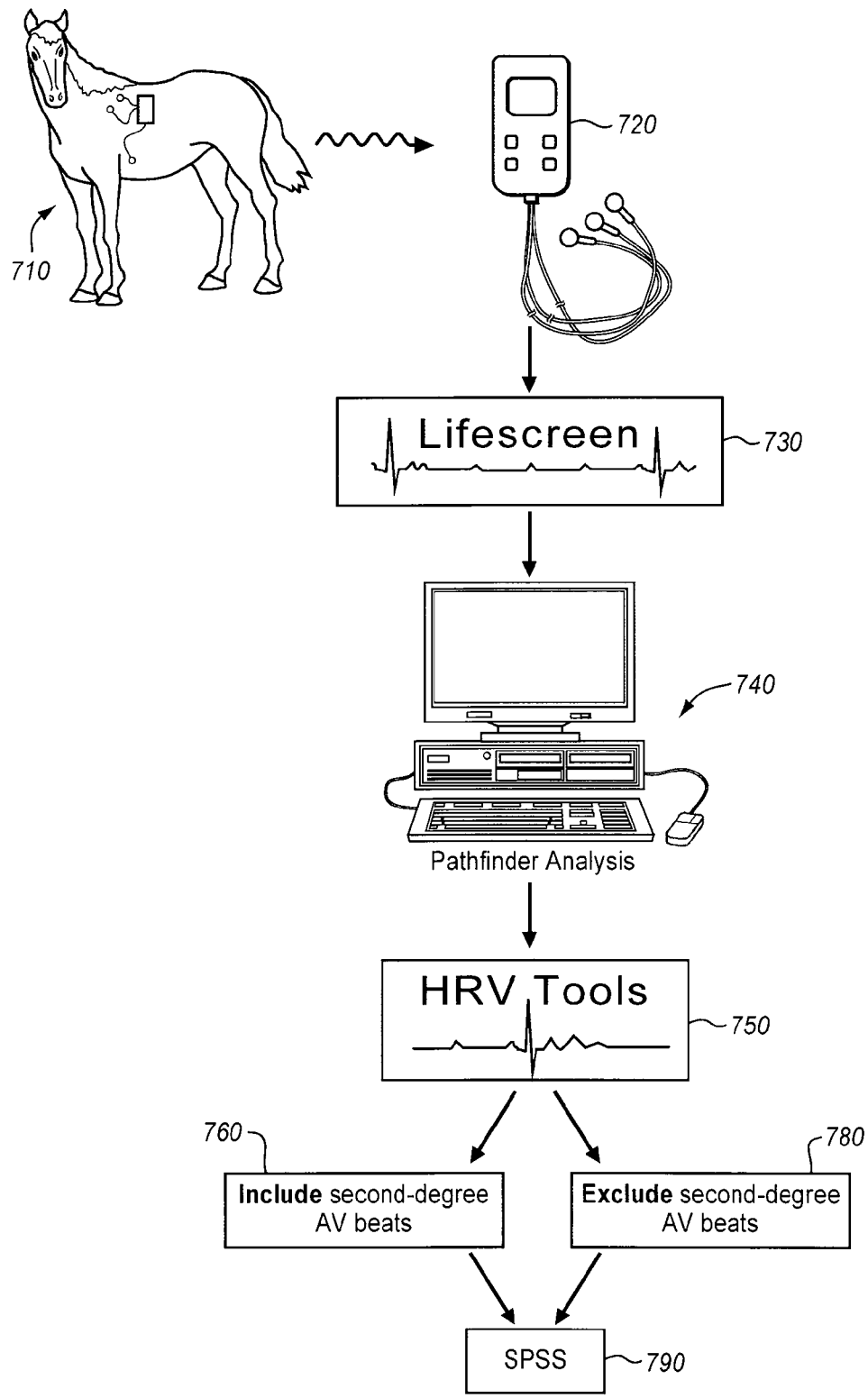
FIG. 7 shows an embodiment of a system for analyzing whether second-degree AV beasts should be included in the HRV analysis.

In one embodiment of the system, multivariate analysis of variance HRV Tools software was used. FIG. 7 shows an embodiment of a system for analyzing whether second-degree AV beasts should be included in the HRV analysis. Similar to previous systems a Lifecard CF Monitor 620 captures information from an animal 710 and the ECG information is processed by Lifescreen 730 and Patherfinder analysis module 740. The data is then processed using HRV analysis was performed using HRV Tools software module 750 (cubic spline resampling, linear subtraction detrending and Hamming windowing). This process is completed in two scenarios, scenario one 760, which includes second-degree AV beats and scenario two 780 which excludes second-degree AV beats. Results of each test in HRV Tools software for each of the three frequency bands and overall total were entered into SPSS 790 (version 13.0) and both SNSI and PNSI indices calculated. Two datasets were generated. The first dataset included overall averages of each filter under the time interval analyzed computed using a GLM with Tukey's Post hoc analysis (01.=0.05) exploring the between-subjects effects of five filters (none, 65-175%, 50-200%, 50-175%, and 65-200%) and overall averaged results of successive segments with five interval lengths of the 30-minute recording (one minute, five minutes, ten minutes, fifteen minutes, and thirty minutes). The second dataset included frequency domain measures Total, VLF, LF, HF, SNSI, and PNSI measures from each segment (of the five-, ten-, and fifteen-minute time intervals) for further analysis with three multivariate GLMs and two Tukey's POSI hoc analyses (ex=0.05) exploring the between-subjects effects across individual segments of different time intervals in the thirty-minute dataset.

The process described in relation to FIG. 7, may be applied to a variety of HRV irregularities and determine on a species (or subspecies) level whether particular irregularities should be included in the temperament analysis.

Caution must be applied when selecting an appropriate filter and time interval in HRV frequency domain analysis to ensure that they effectively capture changes in the temperament of the subject.

Autonomic nervous system (ANS) is representative of changes in an individual horse's internal states. The difference between non-filtered and filtered datasets in "normal" horses suggests caution in the use of filters, as there were differences in PNSI values arising from longer vagally mediated beats. Horse ECG data usually have noise or R on T triggered beats; therefore, a suggested half filter (65%<) would overcome these problems while capturing PNSJ changes which arise from longer beats. Filtering methods of both half filter (65%<) and suggested filter (65-175%) can provide a useful method to investigate the effects of the inclusion/exclusion of second-degree AV blocks on frequency domain, SNSI, and PNSI measures in HRV analysis (Chapter 4). Selection of time intervals influences HRV frequency domain values, with ten-minute segments most effectively capturing shorter and longer cyclical changes of the Fast Fourier transformation.

However, this warrants caution when obtaining an ECG recording of a single ten-minute interval, as parasympathetic system changes occur between the first ten to twenty minutes. A single recording may not capture the change in internal state, as a horse or other mammal appears to adapt in the initial ten-minute period to the experimental procedure and environment. These parasympathetic changes suggest the horse's response to the experimental procedure reflected in their individual ability to adapt to a novel situation and is an important indicator or parameter worth considering when assessing temperament accurately. Fifteen-minute periods are more representative of the individual horse's internal state, accounting for both initial excitement to the experimental setup and adaptation to the environment, both of which are indicative and important when considering equine temperament.

Given the differences found between one-minute intervals and other time intervals sampled, the standardization of human HRV analysis regarding length of time intervals and the exclusion of one-minute intervals are also valid for horses. The lack of difference between five-, ten-, and fifteen-minute time intervals indicates these intervals could be used interchangeably in horse HRV analysis. Differences between the segments of ten- and fifteen-minute time intervals indicated that the selection of interval length reflected changes in the individual mammal during the experimental procedure. While there were visible changes in the frequency domain values for five-minute segments across the thirty-minute dataset, none were statistically valid. However, ten-minute intervals provided a segment length able to capture cyclical components representative of the parasympathetic system, although fifteen-minute intervals would provide a more accurate representation. Past studies suggest horses have a greater parasympathetic measure, justifying the use of longer intervals to attain these longer cyclical components involved in the PNSJ.

A factor that may affect the temperament analysis of FIGS. 1-3 is partial heart block. Partial heart block occurs in mammals, and the effect on the analysis of a particular species is accounted for in one alternative. A problem of assessing the clinical significance of partial heart block in horses has been a controversial subject for many years because missed beats occur at rest in a large number of apparently healthy horses. Atrioventricular (AV) heart block has been defined as an abnormal mechanism in which there is delay in, or absence of, ventricular responses to the auricular impulses. It is reported to be one of the more common disorders of the heartbeat in humans. The exclusion or inclusion of second-degree AV block beats in equine cardio-physiological research is presently under debate. The significance of the AV block varies in species. Both first- and second-degree AV block may be present without outward evidence of cardiac disease. First-degree AV block may result from excessive vagal tone and generally is not considered significant in horses unless other evidence of heart disease is present. In all species, second-degree AV block may be indicative of heart disease.

The effect of the inclusion and exclusion of second-degree AV blocked beats on HRV parameters in the analysis of temperament of mammals is considered in some alternatives. The occurrence and incremental capacity of second-degree AV blocked beats reflects an animal's internal state and regulatory modulation to changes in their environment. Such beats are an indicative parameter of autonomic modulation that varies between individual horses and should be taken into consideration when using HRV to assess equine temperament. The effect of the inclusion or exclusion of second-degree AV blocked beats in equine HRV analysis was through the results as all but VLF values were significantly different. The inclusion of second-degree AV blocked beats supports the theory that second-degree AV blocks are vagally mediated in the horse, as the effect of including these beats lowered the SNSI while elevating the PNSI.

The prevalence of cardiac arrhythmias such as second-degree AV blocks among domestic animals is more common in the horse than in other species and is not clinically significant. Conduction disturbances such as these are considered the waxing and waning of the vagal nerve, which is believed to be the cause of these cardiac irregularities. Although extensive studies have investigated the nature of these beats, equine HRV research has been reluctant to include such beats in data analysis.

Statistical results demonstrated significant differences in HRV parameters between horses indicating that HRV varies from individual to individual, a significant interaction being found between horses and the inclusion or exclusion of second-degree AV block beats in frequency domain values including Total and HF values that are reflective of changes in individual differences in the autonomic modulation of the vagal nerve.

The inclusion of second-degree AV blocked beats gives different values for HRV parameters compared to those obtained when excluded. The results support the inclusion of second-degree AV blocked beats with the use of <65% filter, as such beats are indicative of autonomic modulation of the vagal nerve and varying between individual horses and an important consideration in assessing an individual's temperament.

Biological processes which repeat themselves every 24 hours are called "daily rhythms"; and when these are endogenously generated, but still susceptible to modulation by 24-hour environmental cycles, they are known as "circadian rhythms". Daily oscillation in the levels of physiological variables has been described in a variety of species for a multitude of variables, including locomotor activity, body temperature, HR, blood pressure, hormonal secretion, and urinary excretion. Although circadian periods can be transiently affected by environmental factors, different species tend to have different circadian periods, although there appear to be no idiosyncratic differences between the circadian rhythms of other mammalian species and horses. Environmental factors (such as feeding schedules) place constraints on an animal's behavior but have been shown not to affect circadian rhythms such as equine body temperature. The effect of environmental factors in the circadian rhythms of HRV has not been fully investigated in horses, although human research found a robust daily rhythm of HR, with HRs clearly lower during sleep and rest. However, one study found that horses had marginally elevated HF power at night across the 24 hours, but these findings were not statistically significant. Diurnal variation of HRV in healthy individuals is a normal and reproducible feature, which includes more pronounced interbeat variabilities at night. In humans, there is a distinct day/night difference with maximum variance in the early morning hours just prior to awakening.

Several studies in humans conclude that the rise in HRV at night is mostly attributable to increased vagal tone, whereas changes in variability during the day are due to more complex interactions between sympametic and vagal modulation of SA node activity. Younger healthy subjects exhibit wider fluctuations of interbeat intervals especially at night, while advancing age appears to attenuate the vagal influence and, hence, the extent of HRV across a 24-hour period. On the basis of previous human studies and the knowledge of horses' sleep patterns being different to that of humans, this chapter proposes to investigate whether there are marked day/night differences or diurnal differences which would affect data collection at different times of the day.

Research on circadian rhythms is generally concerned with mean effects rather than individual differences and has focused on the variability between repeated measures on the same individual or between measures of different individuals. This focus has limited the statistical requirement of ascertaining significant differences between means based on the assumption that intra-subject (within the 24-hour period) and inter-subject (between individuals) variabilities are numerically equivalent. However, research has revealed that intra- and inter-subject variability in physiological functions is often different with important implications in both human and clinical practice. If inter-subject variability is greater than intra-subject variability, as in the case of circadian influences in HRV measures across 24 hours, it would imply that individual differences between horses of a group is more influential than the actual time of day of the actual recordings. Conversely, if intra-subject variability is greater than inter-subject variability, the time of day influences will affect the HRV results obtained more than the individual difference between horses. The concepts of intra- and inter-subject variability are two areas which examine the influence of circadian rhythms in HRV results obtained.

In humans, there is a significant circadian variation of HRV with a dominant 24-hour harmonic term, with maximum variation during sleep when the time to peak amplitude ascribed this pattern to vagal influences. The authors postulated that the origin of this circadian variation is likely due to sympathetic withdrawal coinciding with the trough level of circulating catecholamines. A comprehensive study of 50 subjects (age: 37±16 years) without heart disease reported circadian patterns of HRV and found that the HR and total RR interval variability was reduced at night despite an increase in the UF amplitude. An investigation into the 24-hour variation in autonomic modulation in humans found significantly reduced sympathetic modulation (LF power) between 11 pm and 5 am directly opposite the enhanced power contained in the HF (vagal) band. No such changes were found in the present study.

Human studies have also found marked day/night differences; however, the lack of significant findings in this chapter can be either attributed to differences between human and horse sleep patterns or that animals were disturbed throughout the night for data collection. HRV measurements, therefore, may not truly have been made during horses' sleep. A study of 77 healthy human controls found a significant higher HRV at night, especially in the younger subjects. Further investigations by the same authors found the loss of diurnal variation in both HR and HRV during a period of sleep deprivation in eight subjects. Such findings would explain the lack of circadian rhythm in the present study, as the horses' sleep was continuously disturbed. If circadian rhythms are suppressed when sleep is deprived and not disturbing the animal is impossible for data collection, then circadian rhythms are not an overriding influence when recording HRV.

It is worthwhile to remember that HRV, in the final analysis, is an output signal from an exceedingly complex biophysical system. Various computational techniques, some based on non-linear models, are currently being explored to represent the physiological mechanism underlying the day-to-day changes in HRV more faithfully. The present chapter found elevated LF power between the hours of 6 am and 8 am similar to human studies which found HRV has exhibited circadian patterns with the crest of activity occurring between 6 am and 12 noon. Circadian rhythm, strictly speaking, refers to a time event series with a principal frequency of one cycle every 24 to 26 hours. Therefore, to study mechanisms and phenomena involved in circadian rhythms of HRV, a minimum recording time ought to be no less than 48 hours. Had the experiment monitored the horses for a longer period of time, perhaps differences would have become more evident. Yet, the focus of this chapter was not in the investigation of the essential circadian nature but to monitor the presence and effect of such rhythms when sampling at different periods throughout the day. Most time or frequency domain analyses of HRV are derived from RR interval sequences of shorter datasets (2.2 to 5 minutes) or longer datasets (1 minute to 24 hours), both of which provide clues to autonomic balance.

The lack of significance in the results allows the following affirmation that ECG recordings can be taken from individuals throughout different periods of the day and cross-compared without a marked circadian rhythm influencing the data collected. Tests between horses showed significant individual differences between subjects; given the small number of subjects of varied ages and different sexes, no postulations can be made as to whether age or sex were influential factors in this present study.

In determining the temperament of mammals, it is important to isolate the effect of HRV and limit other factors, such as second-degree AV blocked beats (as described above). In horses as well as other mammals, practical difficulties are often encountered when trying to document reliable measures of HRV in field-like conditions, thus yielding questionable results. Previously published techniques have certain limitations associated with them that should be considered and avoided when designing an equine HRV study, thus enabling further investigation of factors which may influence horses' HRV such as age, sex of horse, pregnancy, coat color, diet, stabling, training, exercise, weight, height, and different ratings on a Behavioral Temperament scale. Although these identified factors apply to horses, many of the same factors will apply to humans. For instance, in humans, some factors that are important are age, sex, pregnancy, race, diet, living situation, training, exercise, weight, height, marital status, and behavioral temperament.

Age—The equine central nervous system is not entirely mature at birth, although neurogenesis of the cerebellar cortex is fairly complete in the newborn. There are both morphological and neurochemical features of the equine nervous system that reach maturity at varying developmental stages, yet their functional performance is present at birth.

Consequently, the age of the horse may influence the functioning of the ANS and HRV. As animals age, they experience numerous situations and learn to regulate their response adequately; thus, age must influence HRV in both the sympathetic and parasympathetic interaction and regulation of HRV.

Previous research in horses has demonstrated good stability between individual levels of HRV within age groups. In particular, younger horses (9 months old) had higher HRs than the older groups (21 and 22 months, respectively). Human studies have reopened similar findings, with all time and frequency domain indices of HRV being significantly lower among the older than among the younger individuals. In addition, studies in swine have confirmed that cardiovascular reflexes mature at different postnatal ages, which docs not follow a linear relationship over time.

Sex—Some studies have reported sex differences in ANS regulation of cardiac activity, with females appearing to have higher vagal tone, which is consistent with the sex differences reported in humans. In contrast, an unrelated study using twenty horses failed to observe any sex-based differences, but further work is required to confirm these observations.

Pregnancy—At present, there have been no equine studies conducted to investigate whether pregnant mares have HRs significantly different from those mares which are not pregnant. However, studies in humans have found that the average values of mean RR interval, Total power, and LF component were similar in non-pregnant and normally pregnant women. The HF component was slightly increased in pregnant women but no difference was observed in LF/HF ratio. Given the physiological changes which occur during pregnancy, it is necessary to determine whether pregnancy has an effect in HRV measurements of mares.

Coat color—Although there are no studies involving horses' coat color and HRV, behavioral observations noted marked and significant differences in reactivity of chestnut-color-coated horses in comparison to horses of other coat colors. Observed reactivity has been correlated to HR in horses; higher HRs were associated with more reactive horses. The reactivity of an animal is based on observation; therefore, it is worth further investigation to assess whether coat color influences HRV in horses.

Diet—Significant observations have been made relating nutrition and diet to equine behavior. A grain diet—compared to an alfalfa diet—resulted in a marked increase in crib biting behavior. Alfalfa is commonly fed to horses and is rich in numerous amino acids and other nutrients including both choline and calcium. Human studies have shown how choline has affected HRV measures, increasing time domain measures, while canine studies have demonstrated that an increased cholinergic uptake may cause an increased number of second-degree AV blocks. Lucerne (alfalfa) contains readily available calcium for horses, and calcium ion concentrations have been linked to an increase in LF components of HRV parameters in humans, although there was no marked significant affect.

Stabling—Different backgrounds appear to influence HRV in horses. Stabling rather than background appears directly to influence the horses' behavior, as horses which were housed under group conditions displayed more relaxed behaviors than horses in single stables. Similar results were found in a study investigating stallion housing and behavior; those which were individually housed tended to display more aggressive behavior than those grouped in a bachelor herd. However, a further study showed that, although grouped horses displayed more relaxed behavior, there was no significant difference in HRs compared to those isolated in single stables. Two other studies found contradictory results and concluded that the horse's labile nature predisposed an overreaction to stimuli in a novel stabling environment regardless of whether the individual was housed in group or isolated conditions. Therefore, further work is required to examine different stabling conditions and their effects on horses' HRV to establish the effect of the environment on individual animals.

Training—Although research has not detailed training methods or the type of training administered, it has been noted that untrained horses had higher HRs than those which where trained. Another study found that there was no difference between the HRs of either trained or untrained foals. In general, resting HR in horses is significantly decreased by training but one study has failed to find any training-related changes in the vagal tone when HRV was recorded at rest. Nevertheless, horses which have been handled have shown lower emotionality scores than unhandled individuals. Other work found that under challenging conditions (behavior tests), untrained horses showed more pronounced, though not significant, elevations in HR and associated decreases in HRV parameters.

Exercise—Several horse studies have shown an effect of physical effort and training on cardiac function and sympathovagal balance. Exercise on an aqua-treadmill is associated with significantly higher sympathetic tone and decreased vagal tone. In addition, negative correlations between the immensity of exercise and the overall HRV had been reported, which is likely to be due to a progressive rise in sympathetic tone. Caution must be used when interpreting these results, as the majority of the studies investigated the effects of exercise on heart variability parameters in one horse rather than between horses.

Over a period of time, exercise causes individuals to have lower HRs and higher time domain measurements of HRV. In humans, exercise training has also increased time domain measures of HRV. Until now, there is no published research into the differences between HRV parameters of groups of horses, including fit and exercised versus those that are not. A horse's exercise can be varied and the intensity of each type of exercise complicated to measure; however, horse walkers provide an excellent source of exercise, which can be easily quantified and manipulated.

Weight and Height—To date, research investigating both HR and HRV parameters of body weight in cows has had contradictory results. The HR was higher, and HRV in both time and frequency domains was lower in cows with higher body weights. In contrast, another study found no significant effects of weight on average, minimum, or maximum HRs in cows kept under comparable conditions to the previous study. In horses, weight can prove to be a difficult parameter to estimate accurately, while height is measured as common practice. By taking both weight and height, an accurate assessment of physiological differences attributed to body weight (via a weight band) or height can be assessed against equine HRV.

Behavioral/Temperament Scales—Scientists have observed and requested third parties such as owners, judges, and raters to assess animals using behavioral/temperament scales.

Such methods have been used to quantify behavior, emotionality, reactivity, and temperament in horses and other animals; however, few studies have been cross-validated. Although the studies claim the scales used are representative of and valid for each individual animal, there is a lack of cross-validation or repeated experiments using these scales or matched physiological parameters to support visual observations. One study linked cattle temperament (assessed on a five-point scale) with daily weight gain; further studies have employed this scale or an adapted version and found it a valid measure. Therefore, by using a simple five-point scale adapted from the original proposed by the author for cattle, it is possible to see whether there are significant differences between each of the horses' HRV according to their rating on the scale used. Thus, a physiological measure representative of a horse's autonomic system and representative of the horse's inner state can be linked with the behavioral five-point scale.

In some embodiments, a HRV parameter of adaptability is calculated. At its most fundamental level, an individual's adaptability is the range of an individual's heartbeat divided by its most common heartbeat. In some embodiments, adaptability is measured by using the average mode RR interval within the ECG recording rather than the average calculated mean NN. The range is represented by the standard deviation of RR intervals from the ECG recording (including second-degree AV blocked beats), while the most common heartbeat (RR interval) is not taken as the mean but as the mode. The mode is the most frequently occurring observation and is measured from a RR histogram as the RR interval, which lies on the x-axis with the highest density on the y-axis. The measurement incorporates a novel HRV measure SDMNN (standard deviation of the mode average normal-to-normal intervals), a ratio representative of adaptability, which has not been validated, standardized, or linked to the ANS. The index is a simple ratio with no units. The higher the adaptability index, the more adaptable an individual tends to be.

It is well established that HRV is higher in younger animals. Significant differences in PNSI between horses aged 5 and 6 years old and horses under 3, between 3 and 4, between 10 and 14, and horses 15 and over could be explained by changes which occur in the ANS throughout an individual's life. How horses mature and age neurologically has not been fully investigated; therefore, the discussion of significant findings is speculation based on previous research conducted in humans, rats, and swine.

Cardiovascular reflexes mature at different postnatal ages, and the innervation of the heart occurs at varying times in different species; however, the sequential patterns of innervations are similar. In younger animals, the physiological maturation may only be partly and not entirely responsible for lower parasympathetic nervous system index (PNSI), which can also be a reflection of lack of experience and familiarity.

Studies in horses found that younger animals had elevated HRs compared to older animals (comparison was between 10 to 22 months). The age groups of these studies were not as wide as the Ses Planes population that examined changes in the older animals. As animals age, the ANS becomes mature and experience is gained, explaining higher PNSI, but the lower indices found in animals aged 10 years or more could be attributed to vagal attrition associated with aging. Vagal activity decreases in mature older animals, and such changes would be reflected in PNSI or HRV measures. When considering HRV as a measure to assess equine temperament, the individual's age is an influential factor that must be carefully considered.

Previous studies have found that HRV parameters are influenced by the sex of the horse, with females having higher vagal tone than males.

Pregnancy was investigated with the premise that hormonal changes during pregnancy influence HRV parameters because a human research study found elevated HRV for pregnant women. The results from the present chapter found similar results showing a trend for HRV and a significant difference in PNSI with higher mean differences for pregnant mares compared to non-pregnant individuals and supports the earlier findings. Therefore, pregnancy is an important factor worth consideration when examining an individual mare's HRV parameters, as it has a significant effect in elevating PNSI values and inter-individual differences between mares can be attributed to pregnancy. Two studies noted that chestnut horses were observed as more reactive than horses of other colors. The chestnut horses were different to horses with other colored coats; however, results did show that bay horses had higher VLF power than grey horses. It has been speculated that the VLF power of HRV may be linked to the animal's thermoregulatory capacity. One study investigating coat colors (black, black and white, and white) in cattle found differences in body temperature and shade seeking behavior. Therefore, findings of the present chapter would indicate that bay horses have a higher thermoregulatory capacity than grey horses as reflected by a significantly higher VLF power.

Alfalfa is rich in amino acids and other nutrients including both choline and readily available calcium, and part of the Ses Planes population had alfalfa incorporated into their diets. While calcium ions in human studies have been linked to increasing LF components of HRV parameters, canine studies demonstrated that an increased cholinergic activity caused an increased number of second-degree AV blocks. However, in the Ses Planes population, there was no significant difference between horses which ate alfalfa compared to the other dietary regimes. The lack of findings could be because horses were not fed on exclusively a cereal or forage but a mixture. This does not indicate that nutrition does not have an effect on HR measures, but that in this population there was no effect. Horses housed under different stabling condition in the same study had no differences between HRV measures. Although stabling was different, horses were under the same management and handling criteria; thus, perhaps the differences found in earlier research were due not to differences in stabling but to differences in the surrounding environment or management.

Research in HRV and exercise in the horse has looked at changes in an individual horse's HRV under exercise. However, these studies have not compared measurements at rest between exercised and unexercised horses. The present study did not examine whether training caused changes within an individual horse but whether there were differences between those who were and who were not trained. The comparison between the two groups revealed that there was no difference in HRV measures and autonomic modulation. Baseline measures in this chapter indicate that there is no significant difference in HRV parameters between the exercised and unexercised horses.

An animal's condition is reflected in its weight. Studies in cows, investigating body weight and HRV parameters, have found contradictory results. Cows with higher weights had lower HRV. There was a significant relationship between horses' heights and adaptability indices, but it is difficult to ascertain how height and adaptability are linked.

Horses measuring 1.41 to 1.45 meters had higher adaptability indices than horses of other heights; this was especially marked in comparison to horses that measured 10 cm taller. Within the Arabian horse breed, height does not vary a lot; however, horses of a certain lower height may engage more in manual grooming as their wither height is lower than their taller counterparts. Mutual grooming is a social behavior which horses engage in and has been paired to lowering of HRs which may explain why horses between 1.41 and 1.45 meters have higher adaptability indices of HRV. All of the horses' usual behavior was rated by the stud manager under two circumstances: behavior with humans and behavior with other horses. Under the horses' usual behavior with humans, there were no horses rated as very difficult and agitated; and with the other horses, there were no differences in HRV measures between each group.

Horses rated as agreeable with other horses had higher VLF power than horses rated as submissive and easy going. As discussed before, VLF power is related to thermoregulation rather than autonomic regulation. Therefore, horses rated as agreeable have higher thermoregulatory modulation than their submissive easygoing counterparts. One study in geckos found a relationship between social dominance which interacted with thermal benefits when determining retreat-site selection, as (subordinate) smallest males were forced to use cooler retreat sites when (dominant) larger males were present. Although horses are mammals and geckos are reptiles, the evasion of predators was of higher precedence than thermoregulation. Another study in monkeys and apes found that social partners may be used for thermoregulation. Such findings explain why agreeable (social) horses had the highest VLF power, while other groups had lower measures. Although the VLF component is a HRV measure, it is not under autonomic regulation; therefore, inter-individual differences in autonomic modulation in the population cannot be attributed to the behavior of the horse with other horses but perhaps its thermoregulatory capacity.

In some alternatives, influential factors including age, pregnancy, coat color, height, and ranked disposition with other horses are factored in when evaluating horse temperament based on HRV. Although single factors such as age, pregnancy, coat color, height, and ranked disposition with other horses can be linked with HRV differences, large inter-individual differences in HRV measures cannot be linked to these alone and may be attributed to temperament of the individual animal. Such large inter-individual differences in the results are attributed to individual temperament.

Temperament is defined as biologically rooted constitutional differences of an individual's behavioral tendencies, observed as the consistency of their reactivity, equanimity, and adaptability to their environment. HRV measures are representative of reactivity, equanimity, and adaptability in an individual, thus portraying temperament through numerical values derived from a biological measure.

Reactivity is a noun; the adjective reactive is defined in the Oxford English Dictionary as: a) showing a response to a stimulus; or b) acting in response to a situation rather than creating or controlling it. The sympathetic nervous system mediates neuronal and hormonal stress responses known as the "flight-fight" response and is responsible for regulating many homeostatic mechanisms in living organisms. Sympathetic fibers innervate tissues in almost every organ system and provide diverse regulatory functions including pupil diameter, gut motility, HR, and urinary output among many others. Therefore, the SNSI measured by HRV is a biological measure representative of an individual's reactivity index. The higher the SNSI, the more reactive is an individual's temperament.

Equanimity is a noun defined in the Oxford English Dictionary as calmness or composure. The parasympathetic nervous system is responsible for an animal's equanimity: the parasympathetic nervous system may inhibit or oppose the physiological effects of the sympathetic nervous system and is involved in stimulating digestive secretions, slowing HR, constricting pupils, and dilating blood vessels, and is known as the "rest and digest system". The parasympathetic system conserves an organism's energy as it slows the HR, increases intestinal and gland activity, and relaxes sphincter muscles in the gastrointestinal tract which appear to be in control during "pleasant periods" such as digestion and rest. An individual's equanimity index is represented by the PNSI of HRV measurements.

Adaptability is a noun; the adjective adaptable is defined by the Oxford English Dictionary as able to adjust to or be modified for new conditions or uses. Adaptability has not been linked to a HRV measure representative of either branch of the ANS, as adaptability must reflect the variation or capacity to adjust within the individual. The HRV measurement SDANN (standard deviation of average normal to normal intervals) represents the short and long cyclical variability and measures changes in cycles greater than five minutes in length. The SDANN is the standard deviation of a series of mean values over five-minute periods and uses the average mean NN interval, a numerical value that is a calculated value which is not very representative of the "typical" RR interval of an individual. Therefore, the SDMNN, uses the standard deviation of NN divided by the average mode (the most frequently occurring RR observation) as representative of the adaptability index.

Significant inter-individual differences exist for reactivity, equanimity, and adaptability within a mammal population that cannot be linked to factors such as pregnancy, height, weight, etc. The unique combinations of the three indices (as measured by SNSI, PNSI, and SDMNN) result in the unique temperaments of each mammal. Although these measures have been established as a viable methodology for determining temperament, in alternative embodiments measures of median, frequency, standard deviation, mean, mode, and other statistical studies of features of the ECG may be used, including but not limited to P wave, PR segment, QRS complex, ST segment, T wave, PR interval, ST interval, QT interval, and U wave. Any measurement of the sympathetic nervous system, parasympathetic nervous system and standard deviation of the HRV is a measure of an individual's temperament.

Heart rate variability appears to be a promising indicator of temperament and coping strategies in horses. In humans, a strong relationship was found between parasympathetic nervous system components of HRV and personality. There was an inverse relationship between perceived emotional stress and the HF component, indicating a lower cardiac vagal component of HRV among individuals who were more stressed. This relationship was independent of age, gender, trait anxiety, and cardio-respiratory fitness, and was also independent of HR, mean arterial blood pressure, and respiration rate, factors which can influence HRV.

No study has attempted to interpret HRV parameters as measures representative of temperament, which can numerically quantify and accurately assess any individual. The inter-individual differences in HRV measures including SNSI, PNSI, and SDMNN within a population to temperament have been incorporated to assess temperament accurately with numerical values. Giving temperament numerical values based on biological measures independent of bias or misinterpretation permits cross-cultural and cross-species comparisons. Such numerical values are unique to each individual derived from their ECG recordings and not construed from questionnaires or behavior scales.

Changes in numerical values of one individual can accurately assess the benefits of training, management, or changes in environment reflecting ANS modulation of HRV. It is advantageous to have numerical values of temperament in animal welfare, as this allows stress to be quantified and closely monitored. Numerical values allow identification or grouping of individuals who are predisposed to stable vices and behavioral problems as well as those who have elite performance records.

Figure 8:
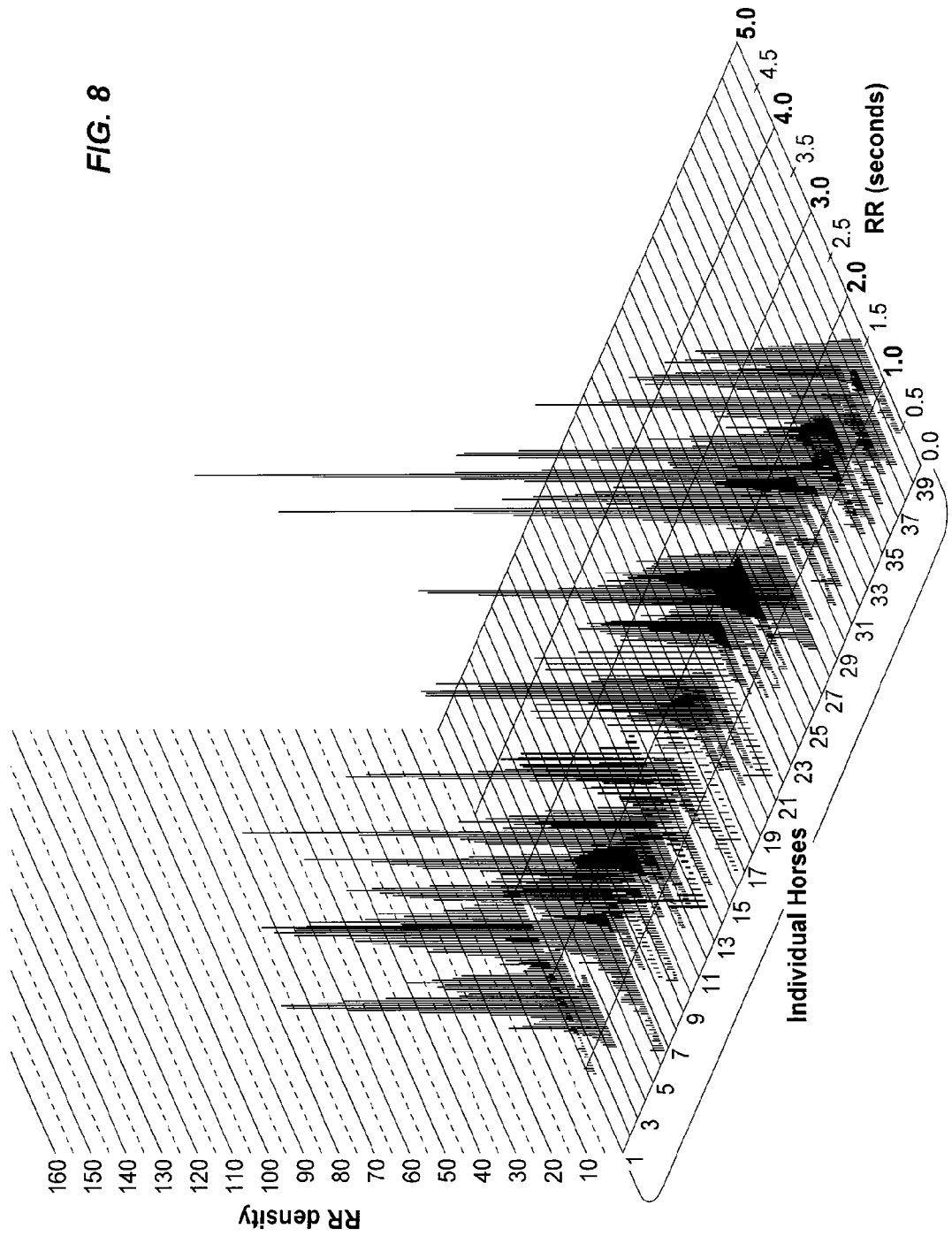
FIG. 8 shows an example of comparing individual horses against each other under a single management.

Representing temperament with numerical values facilitates the comparison of individuals within a population. The advantage of numerical values is vast, both in research in the laboratory and for practical applications in society. Numerical values for temperament enable breed standards and selection criteria involving temperament to have an objective scientific basis, rather than just reflecting the judges' or trainers' preferences. Horses under one management or in one discipline can be compared and ranked against each other, and individual horses can be monitored over a period of time. FIG. 8 shows an example of comparing individual horses against each other under a single management and is a multiple RR Histogram from all 39 horses of Ses Planes Stud.

While all numerical values represent an individual at the given time of the ECG recording, further recordings to confirm values or compare the effects of environment, management, training, or diet would determine as much about the given individual horse as it would about the changing variable. The collection of RR histograms from all of the horses of the Ses Planes population investigated demonstrates the large inter-individual variability of adaptability within the Ses Planes population. The adaptability can be appreciated by looking at both the individual standard deviation (spread) of RR intervals and the individual mode (or height as RR density). The reactivity (SNSI) and equanimity (PNSI) of the same members of the Ses Planes population shows a linear relationship between the two, with those individuals with higher scores for reactivity having lower scores for equanimity and vice versa.

Figure 4:
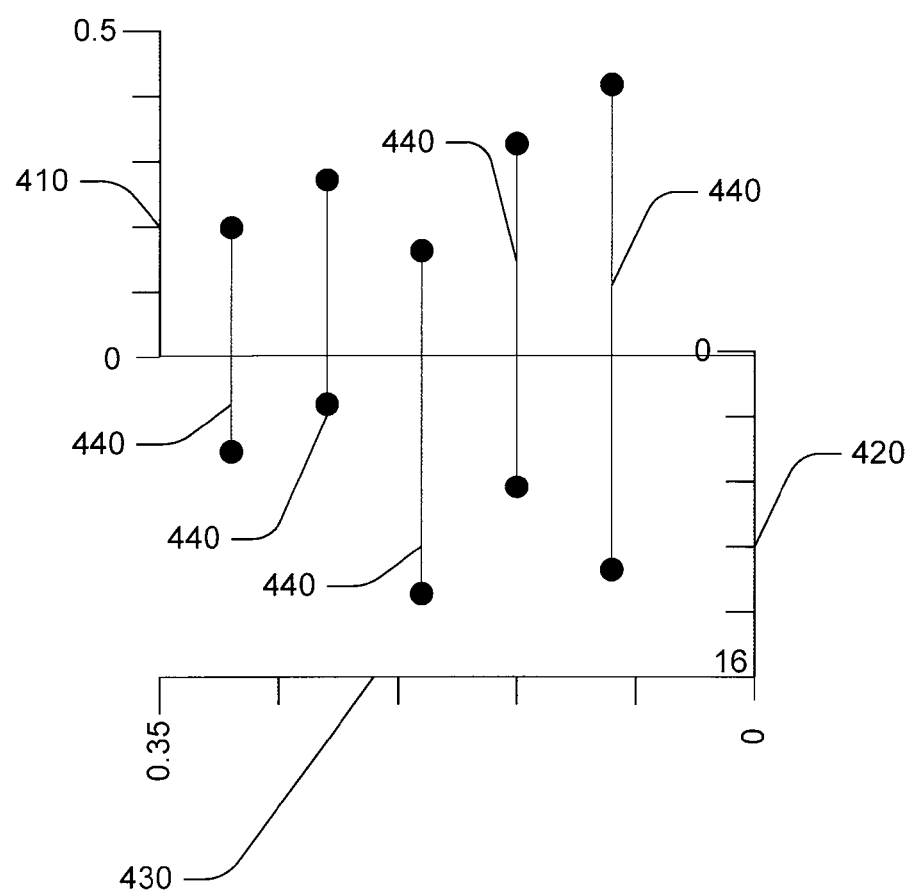
FIG. 4 shows one embodiment of a temperament matrix.
Figure 9:
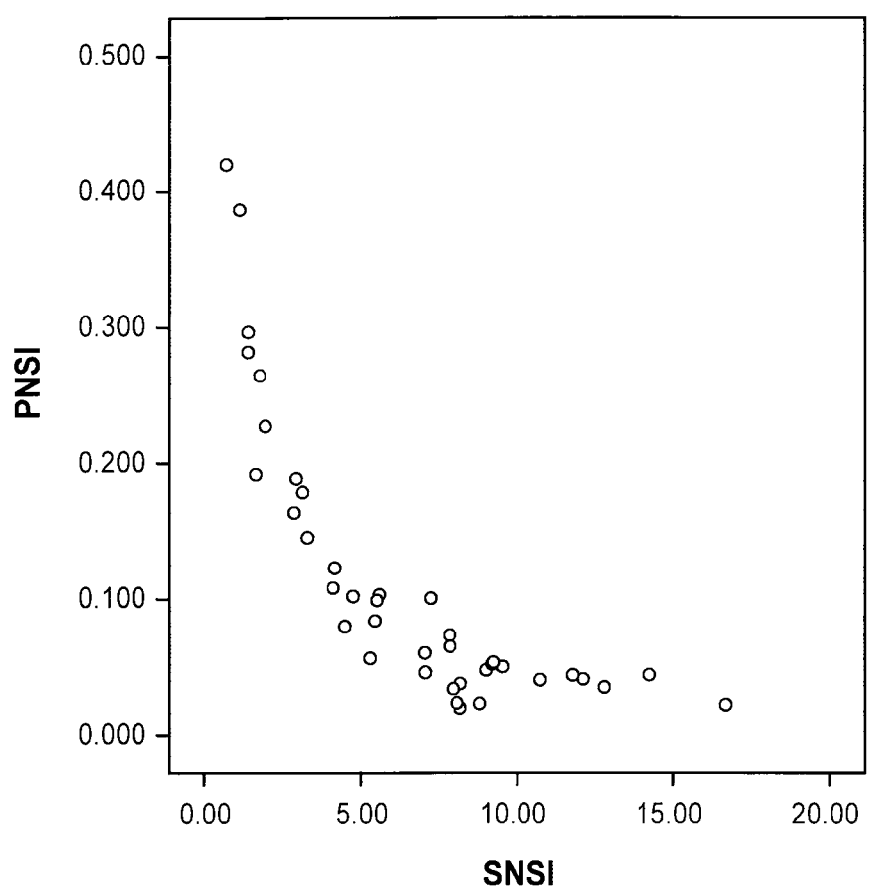
FIG. 9 shows a temperament matrix for Comparative reactivity (SNSI) and equanimity (PNSI) from all 39 horses of Ses Planes Stud.
Figure 10:
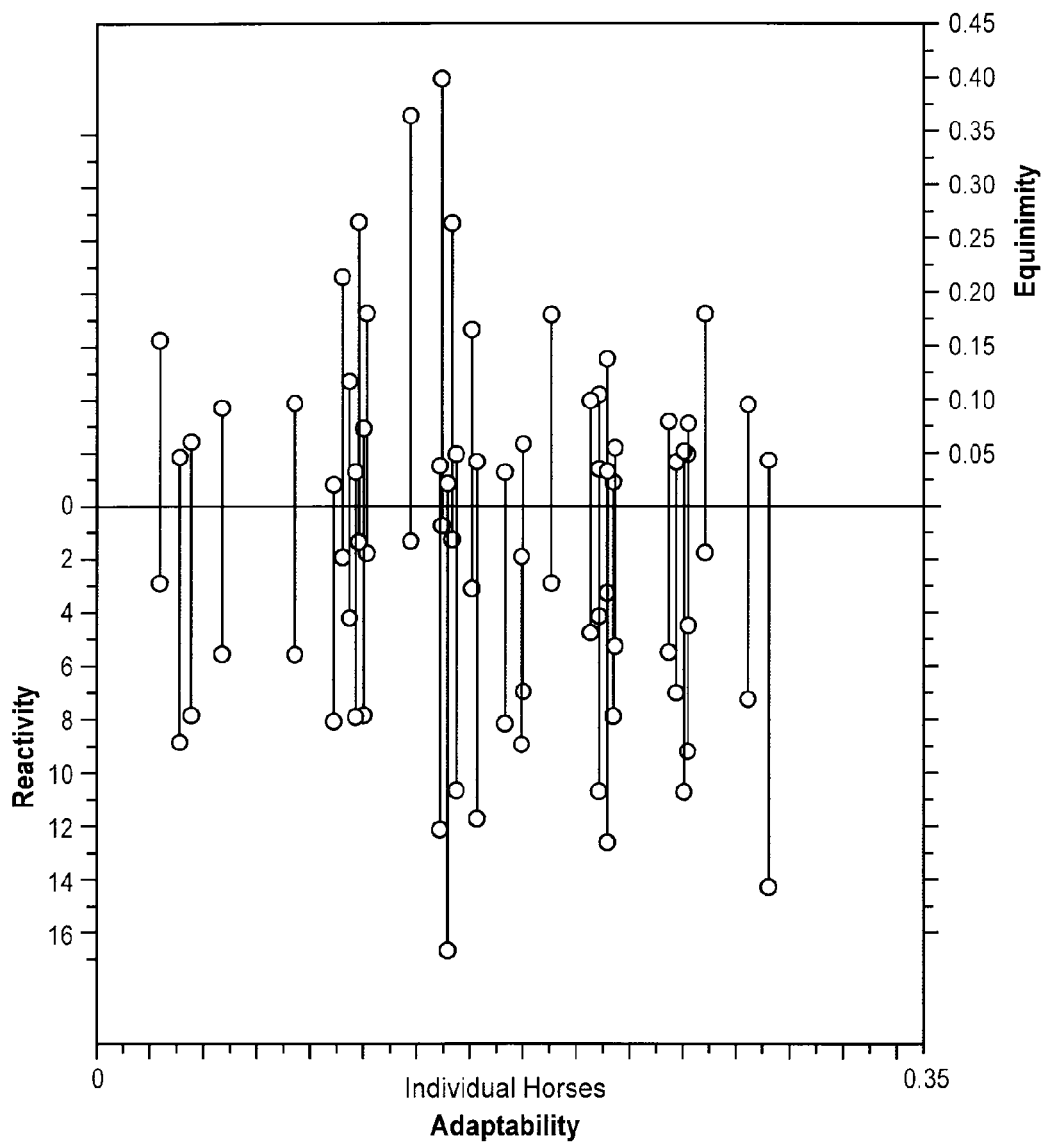
FIG. 10 shows a temperament matrix for Individual temperament (Adaptability Reactivity Equanimity) profiles of Ses Planes population.

Through incorporating the three numerical values representative of the individual's adaptability, reactivity, and equanimity, a unique profile is plotted in a temperament matrix based on three scales. FIG. 4 shows an example of a temperament matrix. The adaptability scale is the x-axis 430, the reactivity scale is the negative y-axis 420, and equanimity scale is the positive y-axis 410, with all three representing the entire state of possibilities in an animal's temperament and places the individual's temperament alongside other members of its population. Each individual has two data points shown as data points 440. FIG. 9 shows a temperament matrix for Comparative reactivity (SNSI) and equanimity (PNSI) from all 39 horses of Ses Planes Stud. FIG. 10 shows a temperament matrix for Individual temperament (Adaptability Reactivity Equanimity) profiles of Ses Planes population.

Figure 5:
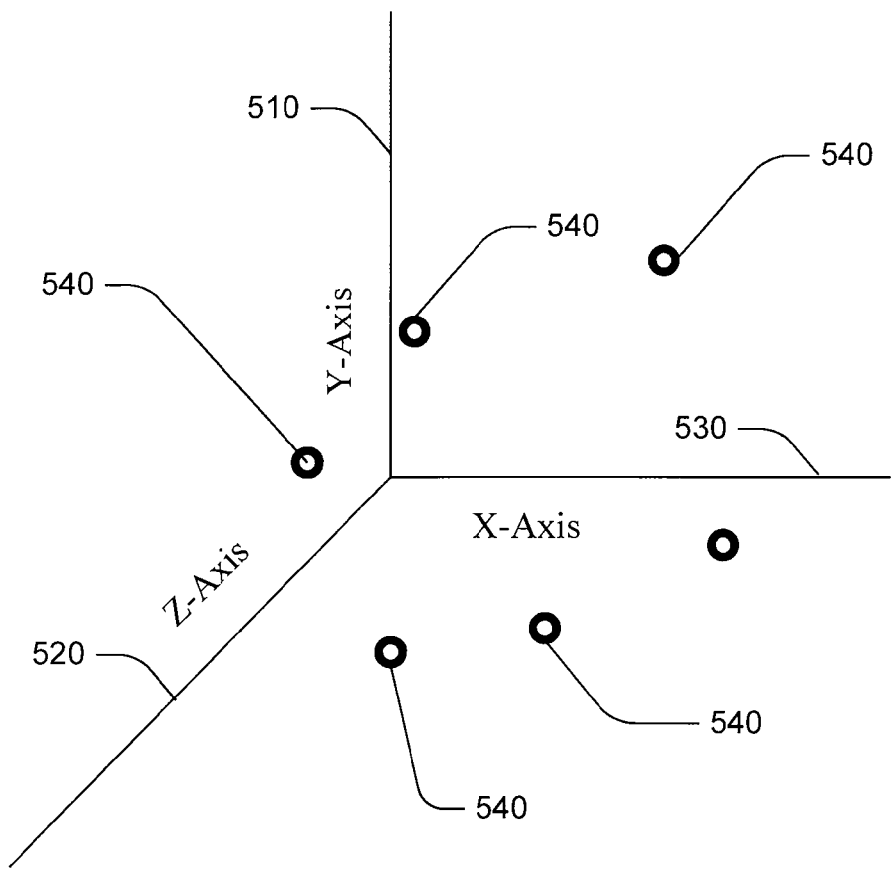
FIG. 5 shows one embodiment of a temperament grid.
Figure 11:
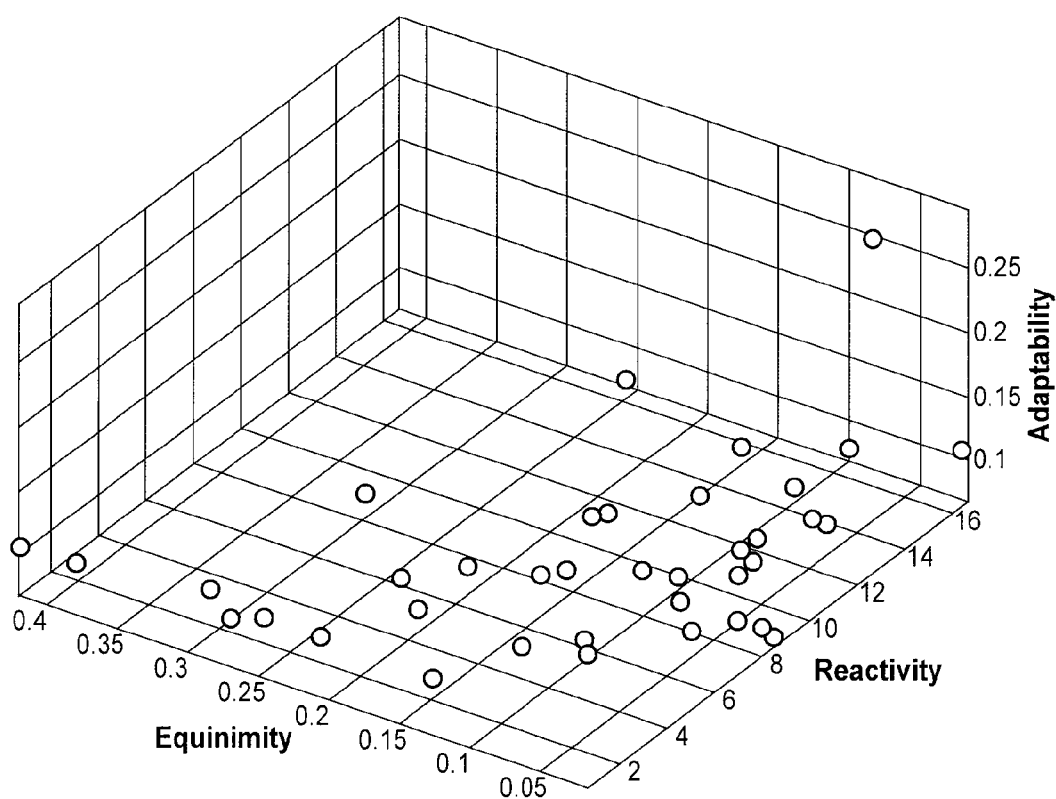
FIG. 11 shows an example of individual horses' temperament position within Ses Planes Population.

The temperament matrix has three independent scales, and individuals were ordered by adaptability scale on the y-axis. FIG. 5 shows an example of a temperament matrix. Y-axis 510 represents adaptability. Z-axis 520 represents reactivity. X-axis 530 represents equanimity. A plurality of data points 540 representing individuals is shown. Such a matrix permits appreciation of different temperament profiles at a glance, while incorporating accurate numerical values facilitating further research in the temperament field. Although there appears to be a linear relationship between reactivity and equanimity, the relationship between reactivity, equanimity, and adaptability together is non-linear, indicating the complex nature of the interactions between these parameters. However, the benefit of graphing the numerical values makes the collection of HRV data for temperament empirical so that the field can advance in a standardized valid manner. FIG. 11 shows an example of individuals horses' temperament position within Ses Planes Population and facilitates of cross comparison of individuals overall position in a population within the temperament grid.

A temperament matrix shows an individual's temperament profiles (adaptability, reactivity, and equanimity) against other individuals within a population. By plotting each individual's adaptability, reactivity, and equanimity as a single point in a temperament grid, rather than a detailed profile in a matrix, different temperaments within a population can be positioned and grouped accordingly. A temperament grid does not look at individual differences but at the population as a whole and provides the range of temperaments within that given population.

Heart rate variability may be used as a means to equine temperament, through adaptability, reactivity, and equanimity measures. These measures provide three independent scales of a temperament matrix for individual profiles and a temperament grid for differences within a population. These measures can be arranged on the basis where one of the A, R or E values are the most important and individuals can be grouped according to preference.

Heart rate variability analysis measures, reflecting autonomic modulation and variation, can be used as representative parameters for reactivity, equanimity, and adaptability of an individual's temperament. The use of a biological measure, such as HRV, to assess temperament (adaptability, reactivity, and equanimity) is advantageous and provides an accurate standardized method with a unique profile for each individual, which can be widely applicable to any animal with a heartbeat.

It should be understood that the particular embodiments described within the specification are for purposes of example and should not be construed to limit the systems and methods which will be described in the claims below. Further, it is evident that those skilled in the art may now make numerous uses and modifications of the specific embodiments described without departing from the inventive concepts. Equivalent structures and processes may be substituted for the various structures and processes described; the subprocesses of the inventive method may, in some instances, be performed in a different order; or a variety of different materials and elements may be used. Consequently, the systems and methods are to be construed as embracing each and every novel feature and novel combination of features present in and/or possessed by the HRV measurement apparatus and methods described.

I claim:

1. A method for assessing temperament in mammals utilizing heart rate variability (HRV), said method comprising:
   determining for a mammal a first HRV value indicative of the reactivity of said mammal based on a HRV measurement, a second HRV value indicative of the equanimity of said mammal based on the HRV measurement, and a third HRV value indicative of the adaptability of said mammal based on the HRV measurement; and
   using said first HRV value, said second HRV value, and said third HRV value to characterize said mammal's temperament, wherein:
   said first HRV value comprises the sympathetic nervous system index (SNSI), said second HRV value comprises the parasympathetic nervous system index (PNSI), and said third HRV value comprises the standard deviation of average mode normal to normal intervals (SDMNN), wherein said average mode is the most frequently occurring observation.

2. A method as in claim 1 wherein said using comprises plotting said first, second, and third HRV values on a three-dimensional grid.

3. A method as in claim 2 wherein said using further comprises comparing said plot on said grid to a reference plot.

4. A measurement tool for assessing a characteristic of a mammal, said measurement tool comprising:
   an electronic heartbeat measurement instrument capable of detecting the electronic pulses created by the beating of a mammal heart and outputting a heartbeat signal characteristic of said mammal beating heart;
   an electrode attachable to said heartbeat measurement instrument;
   an analyzer responsive to said heartbeat signal for determining electronic outputs indicative of three temperament parameters corresponding to the reactivity, equanimity, and adaptability of said mammal; and
   a plotting system for plotting said temperament parameters on a three-dimensional grid.

5. A measurement tool as in claim 4 wherein said analyzer comprises a frequency domain analyzer.

6. A measurement tool as in claim 4 wherein said analyzer comprises a time domain analyzer.

7. A measurement tool as in claim 4 wherein said measurement instrument includes an electronic filter.

8. A measurement tool as in claim 4 wherein said reactivity parameter comprises the heart rate variability (HRV) sympathetic nervous system index (SNSI), said equanimity parameter comprises the HRV parasympathetic nervous system index (PNSI), and said adaptability parameter comprises the standard deviation of average mode normal to normal intervals (SDMNN) of said HRV, wherein said average mode is the most frequently occurring observation.

* * * * *